United States Patent [19]

Farge et al.

[11] Patent Number: 4,526,962
[45] Date of Patent: Jul. 2, 1985

[54] CEPHALOSPORIN DERIVATIVES

[75] Inventors: Daniel Farge; Pierre Le Roy, both of Thiais; Claude Moutonnier, Le Plessis Robinson; Jean-Francois Peyronel, Palaiseau; Bernard Plau, Creteil, all of France

[73] Assignee: Rhone-Poulenc Sante, Courbevoie, France

[21] Appl. No.: 408,712

[22] Filed: Aug. 16, 1982

[30] Foreign Application Priority Data

Aug. 17, 1981 [FR] France .................... 81 15805

[51] Int. Cl.³ .................. C07D 501/20; A61K 31/545
[52] U.S. Cl. ..................................... 544/016; 544/22; 544/26; 544/27; 544/90; 260/239 A; 514/210
[58] Field of Search ................... 544/16, 22, 90, 21, 544/26, 27; 424/246

[56] References Cited

U.S. PATENT DOCUMENTS 4,346,218  8/1982  Tsuji et al. ................... 544/16
4,347,358  7/1982  Bruynes et al. ............... 544/16
4,365,062 12/1982  Farge et al. .................. 544/16

Primary Examiner—Nicholas S. Rizzo
Attorney, Agent, or Firm—Stevens, Davis, Miller & Mosher

[57] ABSTRACT

New cephalosporin derivatives of the formula:

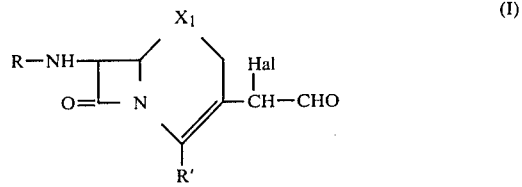

in which R′ represents a protected carboxyl radical, Hal represents a halogen atom, $X_1$ represents a sulphur or oxygen atom or a sulphinyl radical and R represents an acyl radical or an amine-protecting radical, are useful as intermediates for the preparation of cephalosporins having antibacterial activity.

15 Claims, No Drawings

CEPHALOSPORIN DERIVATIVES

The present invention provides the new cephalosporin derivatives of the formula:

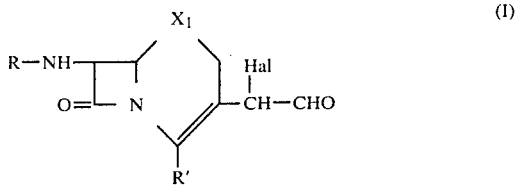

and their isomeric forms and mixtures thereof, in which

R' represents a protected carboxyl radical; Hal represents a halogen atom, such as chlorine, bromine or iodine, and either (A) $X_1$ represents a sulphur or oxygen atom or a sulphinyl radical and R represents a radical of the formula:

[in which $R_1$ is a heterocyclic radical, such as thienyl, furyl or 1,3-dithiol-2-on-4-yl, or a phenyl, free or protected p-hydroxyphenyl or phenoxy radical and $R_2$ is a hydrogen atom, or $R_1$ is a phenyl or free or protected p-hydroxyphenyl radical and $R_2$ is a protected amino radical] or R is an amino-protecting radical which can easily be removed, or (B) $X_1$ represents a sulphur atom and R represents a radical of the formula:
ti R"CO— (II $b_1$)

[in which R" is an alkyl radical of 1 to 7 carbon atoms, or a cycloalkyl, aryl, aralkyl, heteroaryl or heteroaralkyl radical, which is unsubstituted or substituted by one or more halogen atoms or alkyl, alkoxy, alkylthio, halogenoalkyl, azido, cyano, protected amino which is unsubstituted or substituted, protected carboxyl or protected carboxyalkyl radical] or R is a radical of the formula:

[in which m is an integer from 0 to 4, Y is an oxygen or sulphur atom and R" as defined above] or R is a radical of the formula:

[in which R' is as defined above and R'" is a halogen atom or a hydroxyl, protected hydroxyl, azido, acyloxy, protected amino or protected carboxyl radical], or R—NH—represents a sulphonamido group.

It is understood that the alkyl and acyl radicals and portions mentioned above or below are linear or branched and (unless mentioned otherwise) contain 1 to 4 carbon atoms each.

The compounds of the formula (I), which all contain a radical —CH(Hal)—CHO in the 3-position, possess isomeric forms; it is understood that the epimers and mixtures thereof fall within the scope of the present invention.

If $R_2$ is an amino radical or if R is a radical of the general formula (II $b_3$), the substituent in the 7-position of the compounds of the formula (I) exist in the D and L forms; the isomers which result therefrom, and mixtures thereof, fall within the scope of the present invention.

The acid-protecting radical present in R' is a radical which can easily be removed without affecting the rest of the molecule. By way of example, R' can be protected by a t-butyl, methoxymethyl, 2,2,2-trichloroethyl, benzhydryl, p-nitrobenzyl or p-methoxybenzyl radical.

If $R_1$ contains a protected hydroxyl radical, the latter can be protected by any group which is compatible with the preparation and use of the compounds of the general formula (I), e.g. trityl, tetrahydropyranyl, alkoxycarbonyl (t-butoxycarbonyl), aryloxycarbonyl (benzyloxycarbonyl) or p-methoxybenzyl.

If the symbol $R_2$ represents a protected amino radical, it can be protected, e.g. by a t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl or diphenylphosphinoyl group or by a radical such as defined below by the formula (III $a_8$), which group or radical can be introduced by applying the method described by A. Morimoto et al., J. Chem. Soc. Perkin I, 1,109 (1980).

If the symbol R such as defined under (A) represents a protecting radical which can easily be removed, it can be chosen e.g. from amongst:
(1) benzyhydryl or trityl,
(2) an acyl radical of the general formula:

in which $R_3$ represents
(a) a hydrogen atom, an alkyl radical containing 1 to 7 carbon atoms or a methyl radical substituted by 1 to 3 halogen atoms,
(b) a phenyl radical (which can be up to trisubstituted by halogen atoms or hydroxyl, nitro, cyano, trifluoromethyl, alkyl or alkoxy radicals) or a thien-2-yl or thien-3-yl radical,
(c) a radical of the general formula:

in which R'$_3$ is a phenyl radical (which can be substituted by a halogen atom or by an alkyl, alkoxy or hydroxyl radical) and Y is an oxygen or sulphur atom, or
(d) an arylalkyl radical of the general formula:

in which R"$_3$ is a phenyl radical which can be up to trisubstituted by hydroxyl, alkyl or alkoxy radicals, or a heterocyclic radical, such as thien-2-yl or thien-3-yl or furan-2-yl or furan-3yl,
(3) a 5-aminoadipoyl radical, the amine and acid groups of which are protected by protecting radicals such as defined above,
(4) a radical of the general formula:

in which $R_4$ is unsubstituted branched alkyl radical, a linear or branched alkyl radical carrying one or more substituents [such as halogen atoms or cyano, trialkylsilyl or phenyl radicals or phenyl radicals substituted by one or more halogen atoms or by alkyl, alkoxy nitro or phenyl radicals], or a quinolyl radical, and
(5) a radical of the general formula:

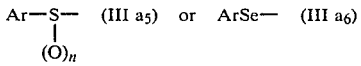

in which formulae the radical Ar is a phenyl radical optionally substituted by one or more halogen atoms or alkyl or nitro radicals, and n is equal to 0 or 1, or alternatively
(6) RNH— can be replaced by a dialkylaminomethyleneamino radical or by a radical of the general formula:

$$Ar'-CH=N- \qquad (III\ a_7)$$

in which Ar' is a phenyl radical optionally substituted by one or more radicals such as alkyl, alkoxy, hydroxyl or nitro, or
(7) R is a diphenylphosphinoyl radical or a radical of the general formula:

in which Z is alkyl, 2,2,2-trichloroethyl, phenyl or benzyl, these last two being optionally substituted by a halogen atom or by an alkyl, alkoxy or nitro radical, or the symbols Z together form an alkylene radical containing 2 or 3 carbon atoms.

The following radicals may be mentioned as examples of protecting radicals R which can be used: formyl, acetyl, trichloroacetyl, phenylacetyl, phenoxyacetyl, benzoyl, t-butoxycarbonyl, 2-chloro-1,1-dimethylethoxycarbonyl, 2,2,2-trichloroethoxycarbonyl, 2,2,2-trichloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl, diphenylmethoxycarbonyl, 2-(biphenyl-4-yl)-isopropoxycarbonyl, quinol-8-yl-oxycarbonyl, o-nitrophenylthio, p-nitrophenylthio, dimethoxyphosphoryl, diethoxyphosphoryl, diphenoxyphosphoryl and dibenzyloxyphosphoryl.

The following may be mentioned as examples of methyleneamino radicals defined above under (6): dimethylaminomethyleneamino, 3,4-dimethoxybenzylideneamino and 4-nitrobenzylideneamino.

By way of example, the symbol R'' defined above can represent, in particular: benzyl, p-hydroxybenzyl, 4-amino-4-carboxybutyl, the amine and acid groups of which are protected, methyl, ethyl, n-amyl, heptyl, 3-nitrobenzyl (or 4-nitrobenzyl), phenethyl, 2-methoxyphenyl, 2,6-dimethoxyphenyl, protected p-aminobenzyl (or protected o-aminobenzyl), p-methoxybenzyl, naphth-1-yl-methyl, isothiazol-3-yl-methyl, isothiazol-4-yl-methyl (or isothiazol-5-yl-methyl), pyridin-4-yl-methyl, isoxazol-5-yl-methyl, benzofuranylmethyl, indol-2-methyl, 3-methylimidazol-1-yl-methyl, 5-methylthien-2-yl-methyl (or 5-methylthien-3-yl-methyl), 5-methoxythien-2-yl-methyl (or 5-methoxythien-3-yl-methyl), 4-chlorothien-2-yl-methyl (or 4-chlorothien-3-yl-methyl), 1,2,5-thiadiazol-3-yl-methyl, 4-methoxy-1,2,5-thiadiazol-3-yl-methyl or tetrazolylmethyl.

If R'' contains a protected amino or carboxyl radical, the latter can be protected by any protection group which is compatible with the reactions used for the preparation and use of the products, and in particular by a protecting group defined for $R_2$, if R'' contains an amino radical, and by a group such as defined above for R', if R'' contains a carboxyl radical.

If the symbol R represents a radical of the general formula (II $b_2$), it can represent e.g. phenoxyacetyl, 3,4-dichlorophenylthioacetyl, pyridin-4-yl-thioacetyl, thiazol-2-yl-thioacetyl or pyrimidin-2-yl-thioacetyl.

If the symbol R represents a radical of the general formula (II $b_3$), the group —CR''R''' can represent e.g. α-hydroxybenzyl, α-amino-3-chloro-4-hydroxybenzyl or α-aminothien-3-yl-methyl.

If RNH— represents a sulphonamido group, it can be e.g. ethylsulphonamido, benzylsulphonamide, 4-chlorophenylsulphonamido or 4-methoxyphenylsulphonamido.

According to the invention, the cephalosporin derivatives of the general formula (I) in which $X_1$ is other than the sulphinyl group can be prepared by reacting a halogenating agent with an enamine of the general formula:

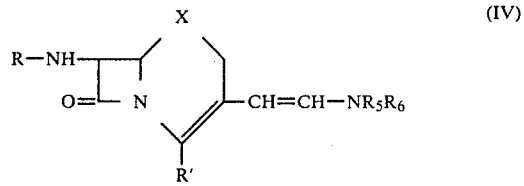

[[in which R and R' are defined as above for the general formula (I), $R_5$ and $R_6$, which are identical or different, represent alkyl radicals (optionally substituted by an alkoxy or dialkylamino radical) or phenyl radicals, or together form, with the nitrogen atom to which they are attached, a 5-membered or 6-membered heterocyclic ring optionally containing another hetero-atom chosen from amongst nitrogen, oxygen or sulphur, and optionally substituted by an alkyl radical, and X is an oxygen or sulphur atom]] and then hydrolysing the product formed.

By way of example an enamine of the general formula (IV) is used in which $R_5$ and $R_6$ are each methyl radical.

The following may be mentioned amongst the halogenating agents: halogens, N-halogenoamides [e.g. N-bromosuccinimide (or N-chlorosuccinimide), N-bromoacetamide (or N-chloroacetamide) and dibromohydantoin] and alkyl hypohalites (e.g. ethyl or t-butyl hypochlorite and t-butyl hypobromite).

The halogenation is generally carried out in an organic solvent, such as an ether (e.g. tetrahydrofuran or dioxane), a chlorinated solvent (e.g. methylene chloride or chloroform), an ester (e.g. ethyl acetate), an alcohol (e.g. methanol or ethanol), an amide (e.g. dimethylformamide or dimethylacetamide), a nitrile (e.g. acetonitrile) or a ketone (e.g. acetone), or in a mixture of such solvents, at a temperature of between −70° and 0° C.

The hydrolysis is carried out at a temperature of between −70° and 20° C.

According to the invention, the products of the general formula (I) in which $X_1$ is a sulphinyl radical can be obtained by oxidising a product of the general formula (I) in which $X_1$ is a sulphur atom.

The reaction is carried out especially under the conditions described in German patent application No. 2,637,176, in particular in the presence of m-chloroperbenzoic acid, in an organic solvent, such as methylene chloride.

The enamines of the general formula (IV) can be prepared by applying the method described in Belgian Pat. No. 883,416, starting from cephalosporin derivatives of the general formula:

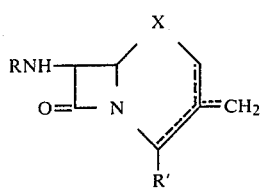
(V)

in which X, R and R' have a corresponding definition.

The cephalosporin derivatives of the general formula (V) in which X is a sulphur atom can be obtained as described in Belgian Pat. No. 833,416 or, if R is a radical which can easily be removed, such as defined above under 7), by applying the method described by A. Morimoto et al., J. C. S. Perkin I, 1,109 (1980), starting from the corresponding halide R-Hal [which can itself be obtained in accordance with one of the methods described by K. Sasse, Methoden der Organischen Chemie (Methods of Organic Chemistry), Volume 12, part 2, page 274, Houben Weyl, Georg Thieme Verlag, Stuttgart (1964)].

The oxacephalosporins of the general formula (V) can be obtained in accordance with the methods described in the literature, e.g.:
in Belgian Pat. Nos. 863,998 and 848,288,
in U.S. Pat. No. 4,108,992, or
by Y. Hamashima et al., Tet. Lett. 4,943 (1979), and
by C. L. Branch et al., J. C. S. Perkin I, 2,268 (1979).
or starting fro the oxacephalosporin of the formula

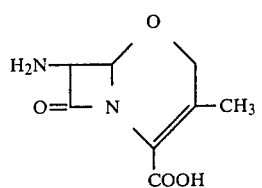
(VI)

by analogy with the methods employed in cephalosporin chemistry and described e.g. by S. Seki et al., Tet. Lett., 33, 2,915 (1977), R. R. Chauvette et al., J. Org. Chem., 38, (17), 2,994 (1973), J. C. Sheehan et al., J. Amer. Chem. Soc. 80, 1,156 (1958), E. H. Flynn, Cephalosporins and Penicillins, Ac. Press (1972), L. Moroder et al., Hoppe Seyler's Z. Physiol. Chem. 357, 1,651 (1976), J. Ugi et al., Angew. Chem. Int. Ed. Engl. 17 (5), 361 (1978), L. Zervas et al., J. Amer. Chem. Soc. 85, 3,660 (1963), J. F. Fitt, J. Org. Chem., 42 (15), 2,639 (1977), A. Morimoto et al., J. Chem. Soc. Perkin I, 1,109 (1980) in Belgian Pat. No. 788,885 or in Helv. Chim. Acta 51, 924 (1968),
if R represents diphenylmethoxycarbonyl: by reaction with the corresponding azidoformate in an aqueous-organic medium, in the presence of an alkali metal bicarbonate,
if R represents quinol-8-yl-oxycarbonyl: by reaction with the corresponding carbonate in a basic aqueous-organic medium,
or if R—NH— is replaced by 4-nitrobenzylideneamino or 3,4-dimethoxybenzylideneamino: in accordance with the method described by R. A. Firestone, Tetrahedron Lett., 375 (1972).

The cephalosporin derivatives according to the invention are useful as intermediates for the preparation of 3-thiazolylcephalosporins of the general formula:

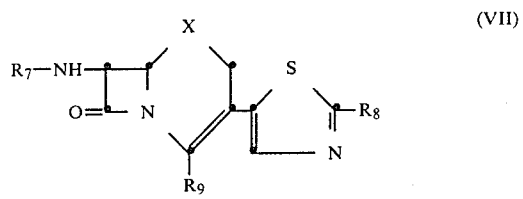
(VII)

in which
($A_1$) the symbol X represents an oxygen or sulphur atom, the symbol $R_7$ represents a radical of the general formula (IIa), in which $R_1$ and $R_2$ are defined as above except that they cannot contain a protected hydroxyl or amino group, the symbol $R_8$ represents a hydrogen atom, a phenyl radical (optionally substituted by an acylamino radical), an alkylthio, alkylamino, dialkylamino, anilino, acylamino, benzoylamino or thienoylamion radical (these last 3 radicals being optionally substituted on the nitrogen atom by an alkyl or phenyl radical), an alkoxycarbonylamino, dialkylaminoethylamino, dialkylaminomethyleneamino or alkylidenehydrazo radical, an acetamido radical substituted by an amino, 2-aminoethylthio or L-2-amino-2-carboxyethylthio radical, or a radical of the structure —AR'$_8$, in which A represents a divalent radical chosen from amongst —CH$_2$—, —NH— or —NHCO— at R'$_8$ represents a 1-methyl-3-pyridinio (or 1-methyl-4-pyridinio, 1-benzoylmethyl-3-pyridinio (or 1-benzoylmethyl-4-pyridinio or 1-carboxymethyl-3-pyridinio (or 1-carboxymethyl-4-pyridinio radical, and the symbol $R_9$ represents a carboxyl radical or represents a carboxylato radical if R'$_8$ is a substituted pyridinio radical, or alternatively
($B_1$) the symbol X represents a sulphur atom, the symbol $R_7$ has one of the meanings given above for R under (B), it being understood that the amino, carboxyl or hydroxyl groups present in certain radicals are in the free state, the symbol $R_8$ represents a hydrogen atom or an alkyl, alkoxycarbonyl, acylamino or dialkylamino radical, and the symbol $R_9$ represents a carboxyl radical.

The products of the general formula (VII) can be obtained from the products of the general formula (I) by the following procedure:
I. If $R_8$ is other than a radical —AR'$_8$,
1. a product of the general formula:

$$R_8—CS—NH_2 \qquad \text{(VIII)}$$

in which $R_8$ is defined as above, it being understood that if it contains an amino radical, the latter is protected, is reacted with a cephalosporin derivative of the general formula (I) [in which R either represents a radical of the general formula (II) or has one of the meanings given above under (B), and $X_1$, Hal and R' are defined as above in the general formula (I)] and then a dehydrating agent is reacted, if appropriate, the sulphoxide obtained is reduced, if necessary, and the protecting groups are removed.

The reaction is generally carried out in an organic or aqueous-organic medium, e.g. in solvents (or mixtures of solvents) such as alcohols (methanol and ethanol), ethers (tetrahydrofuran and dioxane), ketones (acetone), nitriles (acetonitrile), secondary amides (dimethylformamide and dimethylacetamide), esters (ethyl acetate) or acids (acetic acid and formic acid), in the presence or absence of a base (sodium hydroxide, potassium hydroxide, alkali metal carbonates or bicarbonates, alkali metal carboxylates or tertiary amines), at a temperature between −50° C. and the reflux temperature of the reaction mixture.

It is sometimes preferable to introduce a dehydrating agent. This is the case, in particular, if $R_8$ represents a phenyl or substituted phenyl radical.

The following may be mentioned amongst the dehydrating agents which can be used: sulphonic acid halides [e.g. tosyl chloride, methanesulphonyl chloride or a halide of the type $RSO_2Cl$, in which R is alkyl, trifluoromethyl (or trichloromethyl) or phenyl optionally substituted by halogen or nitro], phosphoryl halides (e.g. phosphorus oxychloride) or sulphonyl chloride, either in a basic solvent [pyridine or an amide (e.g. dimethylformamide, dimethylacetamide or hexamethylphosphorotriamide)] or in a chlorinated solvent (e.g. chloroform or methylene chloride), an ether (e.g. tetrahydrofuran), an ester, a ketone, a nitrile or an aromatic solvent, in the presence of a tertiary amine (e.g. pyridine, quinoline or triethylamine).

The reduction of the sulphoxide is carried out, if necessary, in accordance with the methods described in German patent application No. 2,637,176.

The removal of the acid-protecting groups can be carried out e.g.:

in the case of a t-butyl, p-methoxybenzyl or benzhydryl group: by treatment in an acid medium, under the conditions described below for the removal of the amino-protecting trityl radical. In the case of the benzhydryl radical, the reaction can be carried out in the presence of anisole or by treatment with aluminium chloride under the conditions described by T. Tsuji et al., Tet. Lett., 30, 2,793 (1979);

in the case of a methoxymethyl group: by treatment in a dilute acid medium; or in the case of a 2,2,2-trichloroethyl or p-nitrobenzyl group: by reduction (in particular by treatment with zinc in acetic acid or, in the case of the p-nitrobenzyl group, by hydrogenolysis).

The removal of the amine-protecting groups can be carried out e.g.:

in the case of a t-butoxycarbonyl, trityl, p-methoxybenzyloxycarbonyl or formyl radical: by treatment in an acid medium. Preferably trifluoroacetic acid is used, the reaction being carried out at a temperature of between 0° and 20° C., or alternatively anhydrous or aqueous formic, phosphoric or polyphosphoric acid is used, at a temperature of between 20° and 60° C., or para-toluenesulphonic or methanesulphonic acid is used, in acetone or acetonitrile, at a temperature between 20° C. and the reflux temperature of the reaction mixture. Under these conditions, the product of the general formula (I) can be obtained in the form of the trifluoroacetate, the solvate with formic acid, the phosphate, the methanesulphonate or the para-toluenesulphonate, in which the amine group can be freed by any method which is in itself known for obtaining an amine from one of its salts without affecting the rest of the molecule. The reaction can be carried out, in particular, by bringing the product into contact with an ion exchange resin or by reaction with an organic base;

in the case of a 2,2,2-trichloroethoxycarbonyl or p-nitrobenzyloxycarbonyl radical or of a radical of the general formula (III a₈) in which Z is 2,2,2-trichloroethyl or nitrobenzyl: by reduction (in particular by treatment with zinc in acetic acid);

in the case of a chloroacetyl or trichloroacetyl radical: by applying the method described in the French patent published under No. 2,243,199;

in the case of a benzyl or benzyloxycarbonyl radical: by catalytic hydrogenation;

in the case of a trifluoroacetyl radical: by treatment in a basic medium;

in the case of a radical of the general formula (III a₈): in accordance with the method described in Belgian Pat. No. 833,619; or in the case of a diphenylphosphinoyl radical: in accordance with the method described by P. Haake et al., J. Amer. Chem. Soc., 95, 8,073 (1973).

The removal of the protecting groups of the hydroxyl radical is carried out, if necessary:

in the case of a trityl, tetrahydropyranyl or methoxybenzyl group: by acidolysis, e.g. with trifluoroacetic acid, aqueous or non-aqueous formic acid or para-toluenesulphonic acid; or in the case of the alkoxycarbonyl or aryloxycarbonyl groups: in accordance with the methods described in Belgian Pat. No. 871,213.

2. It is also possible to react a product of the general formula (VIII), such as defined above, with a cephalosporin derivative of the general formula (I) in which R represents a protecting radical and X, Hal and R' are defined as above, and then, if appropriate, with a dehydrating agent, in order to prepare a product of the general formula:

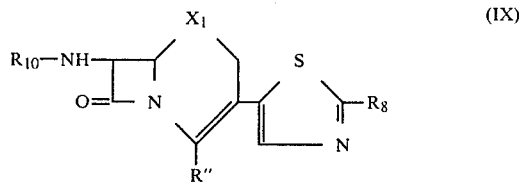

(IX)

in which $X_1$ and $R_8$ are defined as above, R″ is defined in the same way as R' above or represents a carboxyl radical, and $R_{10}$ represents an amino-protecting radical which can easily be removed, such as defined above.

The reaction is carried out under the conditions described above under 1.

If necessary, the removal of the acid-protecting radical is carried out under the condition described above.

The amino-protecting radical $R_{10}$ is then removed, or, if necessary, the protecting radical $R_{10}$ and the protecting radical present in R' are removed simultaneously, from the product of the general formula (IX) in order to prepare a 7-aminocephalosporin (or oxacephalosporin) of the general formula:

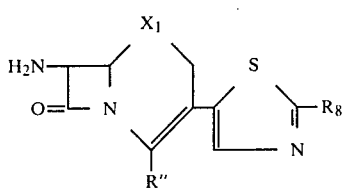

(X)

in which $R_8$ and $X_1$ are defined as above and $R''$ is defined in the same way as $R'$ or represents a carboxyl radical.

The removal of the protecting radical $R_{10}$ is carried out by any known method for freeing an amine group without affecting the rest of the molecule.

The reaction is carried out, in particular, under the conditions described in Belgian Pat. No. 883,415 or described above under 1.

The 7-aminocephalosporin derivative of the general formula (X) is then acylated by means of an acid represented by the general formula:

$$R_7\text{—OH} \qquad (XI)$$

[in which $R_7$ is defined as above and in which, if necessary, the amine group and/or the acid group have been protected beforehand], or by means of a reactive derivative of this acid, and, if necessary, the sulphoxide obtained is reduced and the protecting radicals are then removed.

If $R_7$ contains a hydroxyl radical, the latter can be free or protected by a protecting radical such as defined above.

If $R_7$ contains an amino radical, the latter is protected by a radical such as defined above for $R_2$.

If $R_7$ contains an acid group, the latter is protected by a radical such as defined above.

If the product of the general formula (XI) is used in its acid form, the condensation with the 7-aminocephalosporin of the general formula (X), in which $R''$ is a protecting radical, is carried out in the presence of a condensation agent, such as a carbodiimide (e.g. dicyclohexylcarbodiimide), N,N'-carbonyldiimidazole or 2-ethoxy-1-ethoxycarbonyl-1,2-dihydroquinoline, at a temperature of between $-20°$ and $40°$ C., and the protecting groups are then removed.

If it is desired to use a reactive derivative of the acid of the general formula (XI), it is possible to use the anhydride, a mixed anhydride or a reactive ester of the general formula:

$$R_7\text{—}OZ_1 \qquad (XII)$$

in which, $R_7$ being defined as above, $Z_1$ represents a succinimido, benzotriazol-1-yl, 4-nitrophenyl, 2,4-dinitrophenyl, pentachlorophenyl or phthalimido radical, it being understood that if $R_7$ contains an amino radical, the amine group of all these reactive derivatives is protected beforehand.

It is also advantageous to use an acid halide. In the latter case, if $R_7$ contains an amino group, it is possible to react the hydrochloride of the acid chloride, which, in this particular case, avoids prior protection of the amino radical.

IF the anhydride, a mixed anhydride or an acid halide (which can all be prepared in situ) is used, the condensation is carried out in an inert organic solvent, such as an ether (e.g. tetrahydrofuran or dioxane), a chlorinated solvent (e.g. chloroform or methylene chloride), an amide (e.g. dimethylformamide or dimethylacetamide) or a ketone (e.g. acetone), or in mixtures of the above solvents, in the presence of an acid acceptor, such as an epoxide (e.g. propylene oxide) or such as a nitrogen-containing organic base, e.g. pyridine, dimethylaminopyridine, N-methylmorpholine or a trialkylamine (e.g. triethylamine), or in the presence of a silylating agent, such as bis-trimethylsilylacetamide, or alternatively in an aqueous-organic medium, in the presence of an alkaline condensation agent, such as sodium bicarbonate, and the reaction is carried out at a temperature of between $-40°$ and $40°$ C., and the protecting groups are then replaced by hydrogen atoms.

If a reactive ester of the general formula (XII) is used, the reaction is generally carried out in the presence of a tertiary amine (e.g. triethylamine), in an organic solvent, such as dimethylformamide, at a temperature of between $0°$ and $40°$ C., and the protecting group or groups are then replaced by hydrogen atoms.

The removal of the protecting radicals is carried out under the conditions described above.

The products of the general formulae (VIII) and (XIV), described below, can be prepared by reacting ammonia with the corresponding isothiocyanate or dithiocarbamate, or by reacting hydrogen sulphide with the corresponding nitrile, or, more precisely, in accordance with the methods mentioned below:

if $R_8$ is a hydrogen atom: in accordance with the method described by A. W. HOFMANN, Chem. Ber. 11, 340 (1878);

if $R_8$ is an acylaminophenyl radical: by applying the method of L. Stephesen et al., J. Chem. Soc. (C), 861 (1969);

if $R_8$ represents an alkylthio radical: by reacting ammonium dithiocarbamate with the appropriate alkyl halide;

if $R_8$ represents dialkylamino: by applying the method of MAMELI, Ann. Chimica, 46, 545 (1956);

if $R_8$ represents acylamino: in accordance with the method described by M. L. Moore and F. S. Crossley, J. Amer. Chem. Soc., 62, 3,274 (1940);

if $R_8$ or $R''_8$ represents benzoylamino, thienoylamino, nicotinoylamino or isonicotinoylamino: in accordance with the method of W. H. PIKE, Chem. Ber., 6, 755 (1873);

if $R_8$ represents acylamino, benzoylamino or thienoylamino substituted on the nitrogen atom by an alkyl radical: by analogy with the method described by KURZER, J. Chem. Soc., (1957), 4,461, starting from N-cyanoacetamides, N-cyanobenzamides or N-cyanothienoylamides obtained respectively by applying the method of R. HUFFMANN and F. C. SCHAEFER, J. Org. Chem., 28, 1,816 (1963), or the method of K. HARTKE and E. PALOU, Chem. Ber., 99 (10), 3,155 (1966);

if $R_8$ is an acylamino, benzoylamino ro thienoylamino radical substituted on the nitrogen atom by a phenyl radical: in accordance with the method described by P. K. SRIVASTAVA, Ind. J. Chem., 7 (4), 323 (1969);

if $R_8$ is an alkoxycarbonylamino radical: by applying the method described by R. E. DORAN, J. Chem. Soc., 69, 331 (1896);

if $R_8$ is a dialkylaminoethylamino radical: in accordance with the method described in German Patent Application No. 2,738,711;

if R₈ is a dialkylaminomethyleneamino radical: by applying the method described by H. BREDERECK et al., Ber., 97, 61 (1964); or if R₈ is alkylidenehydrazo: by reacting thiosemicarbazide with the appropriate ketone or aldehyde.

II. If it is desired to obtain a product of the general formula (VII) in which
- (a) R₈ is acylamino, benzoylamino or thienoylamino optionally substituted on the nitrogen atom, alkoxycarbonylamino, dialkylaminomethyleneamino or a substituted acetamido radical,
- (b) R₈ is a radical of the structure —AR'₈ or
- (c) R₈ is an acetamido radical substituted by a 2-aminoethylthio or L-2-amino-2-carboxyethylthio radical,
1. it is also possible to prepare a product of the general formula:

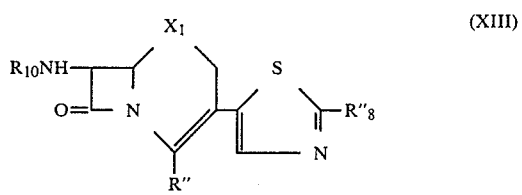 (XIII)

in which $R_{10}$, R" and $X_1$ are defined as above and R"₈ is an amino, alkylamino or phenylamino radical, a radical of the structure:

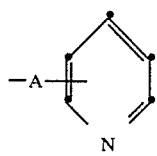

in which A, which is defined as for the general formula (VII), is substituted in the 3-position or 4-position of the pyridyl nucleus, or a halogenoacetamido radical (such as chloroacetamido, bromoacetamido or iodoacetamido), from a product of the general formula (I) in which R is an amino-protecting radical, either by reaction with a product of the general formula:

R"₈CSNH₂ (XIV)

(in which R"₈ is defined as above except that it cannot represent a halogenoacetamido radical) and then, if appropriate, with a dehydrating agent and, if necessary, reduction of the sulphoxide obtained and, if appropriate, removal of the acid-protecting radical, under the conditions defined above under I.1.

or, if R"₈ is a halogenoacetamido radical, from a cephalosporin derivative of the general formula (XIII) in which R"₈ is amino, by reaction with a halogenoacetic acid or one of its derivatives, the reaction being carried out under the acylation conditions defined above under I.2.).

The cephalosporin derivative of the general formula (XIII) is then treated by analogy with the method described under I.2.) for the preparation of a product of the general formula (VII) via cephalosporin derivatives of the general formulae (IX) and (X), so as to give a thiazolylcephalosporin of the general formula:

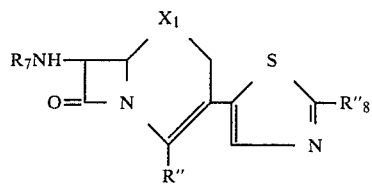 (XV)

in which R", R"₈ and $X_1$ are defined as above and $R_7$ is defined as above, it being understood that if $R_7$ contains an amino radical, the latter is protected, and if R"₈ represents an amino radical, the latter is preferably protected.

The conditions for the introduction and removal of the protecting radicals are identical to those described previously.

The product of the general formula (VII) is obtained by applying one of the following processes, depending on the meaning of R₈:

if it is desired to obtain a product of the general formula (VII) in which R₈ is defined as above under (a) or represents a radical of the structure —AR'₈ in which A is a divalent radical of the structure —NHCO—, a cephalosporin derivative of the general formula (XV) in which R"₈ is an amino, alkylamino or phenylamino radical is converted by any known method for forming an amide, carbamate or amidine group without affecting the rest of the molecule, and then, if necessary, the sulphoxide obtained is reduced and the protectng groups are removed; or if it is desired to obtain a product of the general formula (VII) in which R₈ is defined as above under (b), a methyl, benzoylmethyl or carboxymethyl halide (in which the acid group is free or has been protected beforehand) is reacted with a cephalosporin derivative of the general formula (XV) in which R"₈ is a radical of the structure:

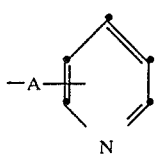

in which A is defined as above, and then, if necessary, the sulphoxide obtained is reduced and, if necessary, the protecting groups are removed.

The reaction is generally carried out in an organic solvent, such as an amide (dimethylformamide, hexamethylphosphorotriamide or dimethylacetamide), a nitrile (e.g. acetonitrile), a ketone (e.g. acetone) or a nitro derivative (e.g. nitromethane or nitrobenzene), or in a mixture of such solvents, at a temperature of between 0° and 80° C.; or if it is desired to obtain a product of the general formula (VII) in which R₈ is defined as above under (c), cysteamine or cysteine, in which the amine group and, if necessary, the acid group have been protected beforehand, is reacted with a cephalosporin derivative of the general formula (XV) in which R"₈ is a halogenoacetamido radical, and then, if necessary, the sulphoxide obtained is reduced and the protecting radicals are removed.

The reaction is generally carried out in an organic solvent, e.g. an amide (dimethylformamide), a nitrile (acetonitrile) or a mixture of such solvents, at a temperature of between −20° C. and the reflux temperature of the reaction mixture. Preferably the reaction is carried out in the presence of a tertiary organic base, e.g. diisopropylethylamine, diethylphenylamine or triethylamine.

If necessary, the reduction of the sulphoxide is carried out in accordance with the methods described in German Patent Application No. 2,637,176.

2. It is also possible directly to prepare a cephalosporin derivative of the general formula (XV) in which $R''_8$ is defined as above except that it cannot represent a halogenoacetamido radical, by reacting a product of the general formula (XIV), in which $R''_8$ is defined as above, with a product of the general formula (I) [in which R either represents a radical of the general formula (IIa) or has one of the meanings given above under (B)], by analogy with the method described above for the preparation of a product of the general formula (XIII) in which $R''_8$ is defined as above.

It is also possible to prepare a product of the general formula (XV) in which $R''_8$ is a halogenoacetamido radical, from the products of the general formula (XV) above, by analogy with the method described above for the preparation of the cephalosporin derivatives of the general formula (XIII).

The products of the general formula (VII) can then be obtained from the cephalosporin derivatives of the general formula (XV), under the conditions described above.

The products of the general formulae (IX), (X), (XIII) and (XV) in which $X_1$ is a sulphinyl radical can be obtained, if appropriate, by oxidising the products of the general formulae (IX), (X), (XIII) and (XV) in which $X_1$ is a sulphur atom, in accordance with the methods described in German Patent Application No. 2,637,176.

The new products according to the present invention and the products of the general formula (VII) can be purified, if appropriate, by physical methods, such as crystallisation, chromatography or ultrafiltration.

The cephalosporin derivatives of the general formula (VII) in which the radicals are defined under ($A_1$) and their pharmaceutically acceptable salts, are particularly valuable antibacterial agents with a narrow spectrum of action, which show a noteworthy in vitro and in vivo activity on Gram-positive germs, particularly on staphylococci and especially on streptococci D.

In vitro, the products of the general formula (VII) have been shown to be active at a concentration of between 0.03 and 8 μg/cc on staphylococci strains sensitive to penicillin G (*Staphylococcus aureus* Smith), at a concentration of between 0.00006 and 0.03 μg/cc on *Streptococcus pyogenes* Dig 7 and *Streptococcus pneumoniae* TIL, and especially at concentrations of between 4 and 60 μg/cc on *Streptococcus faecium* ATCC 9790.

In vivo, the products of the general formula (VII) have been shown to be active at a dose of between 0.01 and 5 mg/kg per day, administered subcutaneously, on the experimental infections caused in mice by *Staphylococcus aureus* Smith.

Furthermore, the $LD_{50}$ of the products of the general formula (VII) is between 0.5 g/kg and doses of more than 2.5 g/kg, administered subcutaneously to mice.

The cephalosporin derivatives of the general formula (VII) in which the radicals are defined under ($B_1$) have been described in French Patent Application No. 2,206,085 as antibacterial agents with a broad spectrum of action, which are active on Gram-positive and especially Gram-negative germs. The said French Application describes the preparation of the cephalosporin derivatives by total synthesis. The synthesis of these products via the products according to the invention is considerably easier.

Of particular value are the products of the general formula (I) in which

A. the symbol X represents an oxygen or sulphur atom, the symbol Hal represents a chlorine, bromine or iodine atom, the symbol R' represents a carboxyl radical protected by a benzhydryl or p-nitrobenzyl group, and the symbol R represents either a radical of the general formula (IIa) in which $R_1$ is phenyl or phenoxy and $R_2$ is a hydrogen atom or, if $R_1$ is phenyl, a protected amino radical, or an amino-protecting radical chosen from amongst t-butoxycarbonyl, trityl or a radical of the general formula (III ag) in which Z is an alkyl radical, or alternatively B. the symbol X represents a sulphur atom and the symbol R represents a radical of the general formula (II $b_1$) in which R" is an aralkyl radical, or R represents a radical of the general formula (II $b_2$) in which m is equal to 0 or 1, Y is an oxygen or sulphur atom and R" is alkyl containing 1 to 7 carbon atoms, aryl or aralkyl, which can be substituted by one or two halogens, or r is a radical of the general formula (II $b_3$) in which R" is aryl and R''' is protected amino.

The examples which follow, which are given without implying a limitation, illustrate the present invention.

EXAMPLE 1

A solution of bromine (0.2 cc) in dry methylene chloride (2 cc) is added dropwise, over a period of 5 minutes, to a solution, cooled to −55° C., of 2-benzhydryloxycarbonyl-7-t-butoxycarbonylamino-3-(2-dimthylaminovinyl)-8-oxo-5-thia-1-azabicyclo[4.2.0]oct-2-ene (E isomer) (2 g) in dry tetrahydrofuran (11 cc). The reaction mixture is stirred for 1 hour at 31 60° C. and then poured into a mixture of ethyl acetate (200 cc) and iced water (200 cc). The organic layer is washed with a semi-saturated solution of sodium bicarbonate (100 cc) and then with water (100 cc) and a semi-saturated solution of sodium chloride (100 cc) and dried over sodium sulphate, in the presence of decolourising charcoal. After filtration, the solvent is evaporated off under reduced pressure (30 mm Hg; 4 kPa) at 30° C. The residue is taken up in isopropyl ether (50 cc), which is evaporated off under reduced pressure (30 mm Hg; 4 kPa) at 30° C. This gives 2-benzhydryloxycarbonyl-3-(1-bromo-2-oxoethyl)-7-t-butoxycarbonylamino-8-oxo-5-thia-1-azabicyclo[4.2.0]oct-2-ene (1.8 g) in the form of a light beige solid (mixture of the two epimers of the bromaldehyde).

Infra-red spectrum ($CHBr_3$), characteristic bands ($cm^{-1}$): 3,420, 1,790, 1,725, 1,505, 1,455, 1,390, 1,370, 1,245, 1,225, 760, 745.

Proton NMR spectrum ($CDCl_3$, 350 MHz, δ in ppm, J in Hz):

epimer A 1.42 (s, 9H, ($CH_3$)C—); 3.71 and 3.55 (AB system, J=17.5, 2H, —$SCH_2$—); 5.06 (d, J=4, 1H, H in the 6-position); 5.22 (d, J=9, 1H, —NH—); 5.65 (dd, J=4 and 9, 1H, H in the 7-position); 6.01 (s, 1H, —CHBr—); 6.99 (5, 1H, —$CHAr_2$); 7.3 to 7.5 (m, 10H, aromatic protons); 9.31 (s, 1H, —CHO).

epimer B 1.42 (s, 9H, (CH$_3$)$_3$C—); 3.35 and 3.65 (AB system, J=17.5, 2H, —SCH$_2$—); 5.01 (D, J=4, 1H, H in the 6-position); 5.29 (d, J=9, 1H, —NH—); 5.72 (dd, J=4 and 9, 1H, H in the 7-position); 6.00 (s, 1H, —CHBr—); 6.92 (s, 1H, —CHAr$_2$); 7.3 to 7.5 (m, 10H, aromatic protons); 9.30 (s, 1H, —CHO).

2-Benzhydryloxycarbonyl-7-t-butoxycarbonylamino-3-(2-dimethylaminovinyl)-8-oxo-5-thia-1-azabicyclo[4.2.0]oct-2-ene (E isomer) can be prepared as described in Belgian Pat. No. 883,415.

EXAMPLE 2

By following a similar procedure to that of Example 1, but treating a solution of 2-benzhydryloxycarbonyl-7-t-butoxycarbonylamino-3-(2-dimethylaminovinyl)-8-oxo-5-thia-1-azabicyclo[4.2.0]oct-2-ene (E form) (21.4 g) in dry tetrahydrofuran (100 cc), at −60° C., with a 10% strength (weight/volume) solution of chlorine in methylene chloride (40 cc), 2-benzhydryloxycarbonyl-7-t-butoxycarbonylamino-3-(1-chloro-2-oxoethyl)-8-oxo-5-thia-1-azabicyclo[4.2.0]oct-2-ene (mixture of the two epimers of the chloroaldehyde) (21.6 g) is obtained.

Infra-red spectrum (CHBr$_3$), characteristic bands (cm$^{-1}$): 3,420, 1,785, 1,720, 1,505, 1,450, 1,390, 1,365, 755, 740.

Proton NMR spectrum (350 MHz, CDCl$_3$, δ in ppm, J in Hz):

epimer A 1.44 (s, 9H, (CH$_3$)$_3$C—); 3.46 and 3.60 (AB system, J=18, 2H, 13 SCH$_2$—); 5.06 (d, J=5, 1H, H in the 6-position); 5.24 (d, J=9, 1H, —NH—); 5.67 (dd, J=5 and 9, 1H, H in the 7-position); 5.90 (s, 1H, —CHCl—); 6.96 (s, 1H, CHAr$_2$); 7.20 to 7.60 (m, 10H, aromatic protons); 9.38 (s, 1H, —CHO).

epimer B 1.44 (s, 9H, (CH$_3$)$_3$C—); 3.23 and 3.63 (AB system, J=18, 2H, —SCH$_2$—); 5.0 (d, J=5, 1H, H in the 6-position); 5.28 (d, J=9, 1H, —NH—); 5.71 (dd, J=5 and 9, 1H, H in the 7-position); 5.94 (s, 1H, —CHCl—); 6.91 (s, 1H, —CHAr$_2$); 7.20 to 7.60 (m, 10H, aromatic protons); 9.45 (s, 1H, —CHO).

EXAMPLE 3

A 0.5 M solution of bromine in methylene chloride (0.08 cc) is added to a solution, cooled to −70° C., of 3-(2-dimthylaminovinyl)-2-(4-nitrobenzyloxycarbonyl)-8-oxo-7-phenylacetamido-5-thia-1-azabicyclo[4.2.0]oct-2-ene (0.02 g) in and the mixture is stirred for 5 minutes at −70° C. The reaction mixture is diluted with ethyl acetate (20 cc) and washed with distilled water (20 cc) and with a saturated solution of sodium cloride (20 cc). The organic solution is dried over magnesium sulphate and concentrated under reduced pressure (30 mm Hg; 4 kPa) at 30° C. This gives a light brown lake (0.02 g) consisting essentially of a mixture of equal proportions of the two epimers (bromoaldehyde) of 3-(1-bromo-2-oxoethyl)-2-(4-nitrobenzyloxycarbonyl)-8-oxo-7-phenylacetamido-5-thia-1-azabicyclo[4.2.0]oct-2-ene.

Proton NMR spectrum (350 MHz, CDCl$_3$, δ in ppm, J in Hz): 3.33 at 3.51 (2d, 1H of the —S—CH$_2$— for the two isomers); 3.57 to 3.77 (mt, the other —H of the —S—CH$_2$— and Ar—CH$_2$—CO—N < for the two isomers); 4.98 and 5.04 (2d, J≈4.5, —H in the 6-position); 5.29 and 5.38+5.30 and 5.39 (4d, J≈12, —COO—CH$_2$-Ar of the two isomers); 5.88 and 5.93 (2dd, J≈4.5 and 9, —H in the 7-position of the two isomers); 6.09 and 6.21 (2s, > CHBr of the two isomers); 7.2 to 7.4 (aromatic protons + — CONH— in the 7-position of the two isomers); 7.56 (d, J≈7.5, aromatic H atoms in the meta-positions to the NO$_2$ of the two isomers); 8.23 (d, J≈7.5, aromatic —H atoms in the ortho-positions to the NO$_2$ of the two isomers);

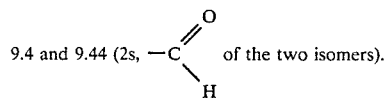

9.4 and 9.44 (2s, —CHO of the two isomers).

EXAMPLE 4

Purified 3-(2-dimethylaminovinyl)-8-oxo-2-(4-nitrobenzyloxycarbonyl)-7-phenoxyacetamido-5-thia-1-azabicyclo[4.2.0.]oct-2-ene (E isomer) (1.4 g) is treated with bromine (0.132 cc), following the procedure described in Example 1, and this gives 3-(1-bromo-2-oxoethyl)-2-(4-nitrobenzyloxycarbonyl)-8-oxo-7-phenoxyacetamido-5-thia-1-azabicyclo[4.2.0.]oct-2-ene (mixture of the epimers of the bromoaldehyde in the proportions 50/50) (1.4 g) in the form of a hard beige foam.

Proton NMR spectrum (350 MHz, CDCl$_3$, δ in ppm, J in Hz): 3.39 and 3.68+3.57 and 3.78 (2 sets of 2d, J≈18, 2H, —S—CH$_2$—); 4.57 (s, 2H, —O—CH$_2$—CO— of the two isomers); 5.05 and 5.11 (2d, J≈5, 1H, —H in the 6-position); 5.32 and 5.41+5.33 and 5.42 (2 sets of 2d, J≈13, 2H, —COOCH$_2$—); 5.96 and 6.02 (2dd, J≈5 and 9, 1H, —H in the 7-position); 6.11 and 6.22 (2s, 1H, >CHBr); 6.93 (d, J≈7.5, 2H, aromatic protons in the ortho-positions of the phenoxy); 7.05 (t, J≈7.5, 1H, aromatic proton in the para-position of the phenoxy); 7.33 (t, J≈7.5, +d, J≈9, 3H, aromatic protons in the meta-positions of the phenoxy+ —CO—NH—); 7.59 and 7.60 (2d, J≈7.5, 2H, aromatic protons in the meta-positions to the nitro); 8.23 (d, J≈7.5, 2H, aromatic protons in the ortho-positions to the nitro);

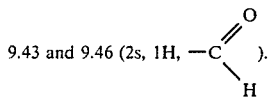

9.43 and 9.46 (2s, 1H, —CHO).

EXAMPLE 5

A solution of bromine (1.72 g) in dry methylene chloride (7 cc) is added, over a period of 10 minutes, to a solution, cooled to−78° C., of the E isomer of 2-benzhydryloxycarbonyl-3-(2-dimethylaminovinyl)-8-oxo-7-tritylamino-5-oxa-1-azabicyclo[4.2.0]oct-2-ene. (7.14 g) in dry tetrahydrofuran (50 cc); the mixture is stirred for 10 minutes at −78° C., the temperature is then allowed to rise to −40° C. and distilled water (0.39 cc) is added. After 10 mixtures, an aliquot (5 cc) of the reaction mixture is removed and diluted in ethyl acetate (10 cc). This organic phase is washed with distilled water (5 cc) and then with a semi-saturated solution of sodium chloride (5 cc). It is then dried over anhydrous sodium sulphate and concentrated to dryness under reduced pressure (30 mm Hg; 4 kPa) at 20° C. The residue (0.61 g) is chromatographed on a column (height: 21 cm; diameter: 1.8 cm) of silica gel (0.04–0.06 mm), elution being carried out under 40 kPa with a 75/25 (by volume) cyclohexane/ethyl acetate mixture, and 25 cc fractions being collected. Fractions 3 and 4, containing a mixture of the epimers of 2-benzyhydryloxycarbonyl-3-(1-bromo-2-oxoethyl)-8-oxo-7-tritylamino-5-oxa-1-azabicyclo[4.2.0]oct-2-ene, are combined and concentrated to dryness under reduced pressure (30 mm Hg; 4 kPa) at 20° C. This gives a mixture of the two bromoaldehydes (0.03 g) in the from of a hard brown foam.

Positions of the characteristic peaks of the proton NMR spectrum (350 MHz, CDCl$_3$, δ in ppm, J in Hz): 6.22 and 6.41 (s, 2H, >CHBr); 9.27 (s, 2H, —CHO).

The E form of 2-benzhydryloxycarbonyl-3-(2-dimethylaminovinyl)-8-oxo-7-tritylamino-5-oxa-1-azabicyclo[4.2.0] oct-2-ene can be obtained in the following manner:

A solution of 2-benzhydryloxycarbonyl-3-methyl-8-oxo-7-tritylamino-5-oxa-1-azabicyclo[4.2.0]oct-2ene (4.25 g) in dimethylformamide (20 cc) is heated to 80° C. under nitrogen. t-Butoxy-bis-dimethylaminomethane (1.55 cc) is added dropwise, over a period of 7 minutes, to the solution stirred at 80° C. When the addition has ended, the mixture is stirred at 80° C. for 17 minutes. The solution is diluted with ethyl acetate (150 cc), the organic phase is washed with distilled water (3×60 cc) and a semi-saturated solution of sodium chloride (60 cc), dried over sodium sulphate and filtered, and the filtrate is concentrated to dryness at 30° C. under reduced pressure (20 mm Hg; 2.7 kPa). The residue is triturated in ethyl ether (150 cc), the suspension obtained is filtered and the filtrate is concentrated to dryness at 30° C. under reduced pressure (20 mm Hg; 2.7 kPa). This gives a crude product (3.14 g) consisting mainly of the E form of 2-benzhydryloxycarbonyl-3-(2-dimethylaminovinyl)-8-oxo-7-tritylamino-5-oxa-1-azabicyclo-[4.2.0]oct-2-ene, which can be used without further purification.

Infra-red spectrum (KBr), characteristic bands (cm$^{-1}$): 1,780, 1,660, 1,615, 1,490, 1,450, 745, 700.

Proton NMR spectrum (350 MHz, CDCl$_3$, δ in ppm, J in Hz): 2.77 (s, 6H, —N(CH$_3$)$_2$); 3.71 (d, J=3.5, 1H, H in the 6-position); 4.12 and 4.53 (2d, J=17, 2H, —CH$_2$—O—); 4.26 (b, 1H, H in the 7-position); 6.24 and 6.40 (2d, J=13, 2H, —CH=CH—); 6.81 (s, 1H, —COO—CH(C$_6$H$_5$)$_2$).

2Benzhydryloxycarbonyl-3-methyl-8-oxo-7-tritylamino-5-oxa-1-azabicyclo[4.2.0]oct-2-ene (7.74 g) is prepared in accordance with a synthesis scheme described in U.S. Pat. No. 4,108,992, in which the t-butyl glyoxylate is replaced by benzhydryl glyoxylate prepared according to French Pat. No. 1,495,047.

The expected oxacephalosporin is obtained in the form of a white solid from 3-tritylamino-4-(prop-2-ynyloxy)2-oxoazetidine (13.2 g).

Infra-red spectrum (KBr), characteristic bands (cm$^{-1}$): 3,340, 1,780, 1,715, 1,620, 1,595, 1,585, 1,490 1,450, 1,220, 745, 700.

Proton NMR spectrum (350 MHz, CDCl$_3$, ≃ in ppm, J in Hz): 1.90 (s, 3H, —CH$_3$); 3.75 (d, J=3.5, 1H, H in the 6-position); 3.87 and 4.08 (2d, J=18, 2H, —CH$_2$—O—); 4.30 (d, J=3.5, 1H, H in the 7-position); 6.85 (s, 1H, —COO—CH(C$_6$H$_5$)$_2$); 7.15 to 7.4 (m, 26H, aromatic protons and —HN—C(C$_6$H$_5$)$_3$).

EXAMPLE 6

Following the procedure of Example 1, 2-benzhydryloxycarbonyl-3-(2-dimethylaminovinyl)-7-diethoxyphosphorylamino-8-oxo-5-thia-1-azabicyclo[4.2.0]oct-2-ene (E isomer) (2.3 g) in dry tetrahydrofuran (12 cc) is treated with a solution of bromine (0.2 cc) in methylene chloride (0.8 cc) and the reaction mixture is then poured into a mixture of ethyl acetate (40 cc) and iced water (100 cc). The organic layer is washed with iced water (3×50 cc) and then dried over magnesium sulphate. After evaporation of the solvent under reduced pressure (30 mm Hg; 4 kPa) at 30° C., 2benzhydryloxycarbonyl-3-(1-bromo-2-oxoethyl)-7-diethoxyphosphorylamino-8-oxo-5-thia-1-azabicyclo[4.2.0]oct-2-ene (mixture of the diastereoisomeric bromoaldehydes) (2.49 g) is obtained in the form of a hard beige foam.

Infra-red spectrum (CHBr$_3$), characteristic bands (cm$^{-1}$): 3,380, 2,730, 1,785, 1,720, 1,490, 1,245, 1,020, 975, 760, 740.

Proton NMR spectrum (350 MHz, CDCl$_3$, δ in ppm, J in Hz): mixture of two diastereoisomers in the proportions 55/45 (A/B): 1.30 to 1.40 (m, ≃6H, —CH$_3$ of A and B); 3.36 and 3.68 + 3.53 and 3.74 (2 sets of 2d, J≃18, —CH$_2$S— of A and B);

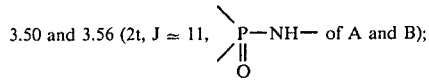

3.50 and 3.56 (2t, J ≃ 11, \P—NH— of A and B);
            /∥
            O 4 to 4.2 (m, ≃4H, —O—CH$_2$— of A and B); 5.01 and 5.06 (2d, J≃5, —H in the 6-position of A and B); 5.16 and 5.24 (2dt, J≃5 and 11, 2H, —H in the 7-position of A and B); 5.97 (s, 1H, >CH—Br of A and B); 6.90 (s, —COO—CH(C$_6$H$_5$)$_2$ of B); 6.97 (s, —COO—CH(C$_6$H$_5$)$_2$ of (A); 7.25 to 7.45 (m, aromatic protons of A and B);

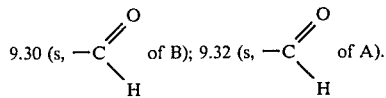

9.30 (s, —C(=O)H of B); 9.32 (s, —C(=O)H of A).

2-Benzhydryloxycarbonyl-3-(2-dimethylaminovinyl)-7-diethoxyphosphorylamino-8-oxo-5-thia-1-azabicyclo[4.2.0]oct-2-ene (E isomer) can be prepared in the following manner:

t-Butoxy-bis-dimethylaminomethane (6 cc) is added to a solution of 2-benzhydryloxycarbonyl-7-diethoxyphosphorylamino-3-methyl-8-oxo-5-thia-1-azabicyclo[4.2.0]oct-2-ene (10 g) in dry N,N-dimethylformamide (100 cc) at 80° C. After 12 minutes at 80° C., the reaction mixture is poured into ethyl acetate (400 cc) and washed with distilled water (5×250 cc). After drying over magnesium sulphate and evaporation of the solvent under reduced pressure (30 mm Hg; 4 kPa) at 30° C., 2-benzhydryloxycarbonyl-3-(2-dimethylaminovinyl)-7-diethoxyphosphorylamino-8-oxo-5thia-1-azabicyclo[4.2.0]oct-2-ene (E isomer) (10.5 g) is obtained in the form of an orange crystalline solid. This product is purified by crystallisation from ethyl acetate (30 cc), and 2-benzhydryloxycarbonyl-3-(2-dimethylaminovinyl)-7-diethoxyphosphorylamino-8-oxo-5-thia-1-azabicyclo [4.2.0]oct-2-ene (E isomer) (5.3 g) is obtained in the form of a yellow crystalline powder (m.p.=193°-194° C.).

Infra-red spectrum (CHBr$_3$), characteristic bands (cm$^{-1}$): 3,370, 3,320, 2,800, 1,760, 1,680, 1,610, 1,530, 1,230, 1,010, 970, 750.

Proton NMR spectrum (350 MHz, CDCl$_3$, δ in ppm, J in Hz): 1.35 and 1.40 (2t, J≃7, 6H, —CH$_3$); 2.90 (s, 6H, —N(CH$_3$)$_2$): 3.08 and 3.18 (2d, J≃15, 2H, —S—CH$_2$—);

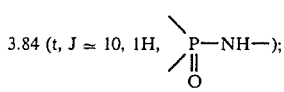

4.15 and 4.22 (2q, J≃7, 4H, —OCH₂—); 4.81 (dt, J≃4.5 and 10, 1H, —H in the 7-position); 5.08 (d, J≃4.5, 1H, —H in the 6- position); 6.53 and 6.78 (2d, J≃14, 2H, —CH=CH—N <); 6.88 (s, 1H, —COO—CH(C₆H₅)₂); 7.20 to 7.50 (m, 10H, aromatic protons).

2-Benzhydryloxycarbonyl-7-diethoxyphosphorylamino-3-methyl-8-oxo-5-thia-1-azabicyclo[4.2.0]oct-2-ene can be prepared in accordance with the method of A. MORIMOTO, J. C. S. Perkin I, 1109 (1980).

EXAMPLE 7

Following the procedure of Example 2, a solution, cooled to −70° C., of 2-benzhydryloxycarbonyl-7-diethoxyphosphorylamino-3-(2-dimethylaminovinyl)-8-oxo-5-thia-1-azabicyclo[4.2.0]oct-2ene (E isomer) (7.3 g) in dry tetrahydrofuran (36 cc) is treated with a 5% strength solution of chlorine in methylene chloride (18.4 cc). This gives 2-benzhydryloxycarbonyl-3-(1-chloro-2-oxoethyl)-7-diethoxyphosphorylamino-8-oxo-5-thia-1-azabicyclo[4.2.0]oct-2-ene (mixture of the diastereoisomers of the chloroaldehyde) (7 g) in the form of a hard orange foam.

Infra-red spectrum (CHBr₃), characteristic bands (cm⁻¹): 3,380, 2,730, 1,785, 1,720, 1,490, 1,245, 1,020, 975, 760, 740.

Proton NMR spectrum (350 MHz, CDCl₃, δ in ppm, J in Hz): mixture of the two diastereoisomers in the proportions 55:45 (A and B): 1.30 to 1.40 (m, δ6H, —CH₃ of A and B); 3.23 and 3.64+3.51 (2d, J≃18, + limiting AB, J≃18, 2H, —CH₂—S— of A and B);

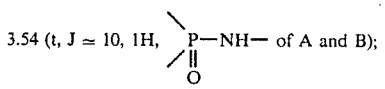

4.03 to 4.17 (m, ≃4H, —O—CH₂— of A and B); 4.98 and 5.05 (2d, J≃5, 1H, —H in the 6-position of A and B); 5.17 and 5.25 (2dt, J≃10 and 5, H in the 7-position of A and B); 5.87 (s, >CH—Cl of B); 5.91 (s, >CH—Cl of A); 6.90 (s, —COO—CH(C₆H₅)₂ of B); 6.95 (s, —COOCH(C₆H₅)₂ of A); 7.25 to 7.50 (m, aromatic protons of A and B);

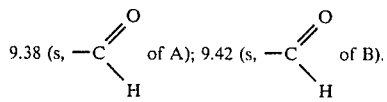

EXAMPLE 8

A solution of N-bromosuccinimide (0.89 g) in tetrahydrofuran (20 cc) is added, over a period of 25 minutes, to a solution of 2-benzhydryloxycarbonyl-7-t-butoxycarbonylamino-3-(2-dimethylaminovinyl)-8-oxo-5-thia-1-azabicyclo[4.2.0]oct-2-ene (E isomer) (2.67 g) in tetrahydrofuran (30 cc), cooled to −20° C. The reaction mixture is stirred for 30 minutes at −20° C. and then concentrated to dryness under reduced pressure (30 mm Hg; 4 kPa) at 30° C.

The residue obtained is chromatographed on a column (height: 22 cm, diameter: 4.4 cm) of silica gel (0.04–0.06 mm), elution being carried out under a pressure of 0.4 bar with a mixture of cyclohexane and ethyl acetate (60/40 by volume), and 50 cc fractions being collected. Fractions 3 to 6, containing the pure product, are combined and concentrated to dryness under reduced pressure (30 mm Hg, 4 kPa) at 30° C. This gives 2-benzhydryloxycarbonyl-3-(1-bromo-2-oxoethyl)-7-t-butoxycarbonylamino-8-oxo-5-thia-1-azabicyclo[4.2.0]oct-2-ene (mixture of epimers of the bromoaldehyde) (1.3 g) in the form of a hard orange foam, the infra-red and proton NMR spectra of which are identical to those of the product described in Example 1.

The examples which follow illustrate the preparation and use of the products according to the invention, it being unnecessary to isolate the product of the general formula (I) in order to use it in a new reaction stage.

EXAMPLE 9

A suspension of iodine (2.54 g) in dry methylene chloride (20 cc) is added, over a period of 5 minutes, to a solution, cooled to −55° C., of the E form of 2-benzhydryloxycarbonyl-7-t-butoxycarbonylamino-3-(2-dimethylaminovinyl)-8-oxo-5-thia-1-azabicyclo[4.2.0]oct-2-ene (5.35 g) in dry tetrahydrofuran (20 cc). The reaction mixture is stirred for 2 hours, the temperature being allowed to rise gradually to 0° C., and then treated with distilled water (0.36 cc) and stirred for 2 hours at +5° C. A solution of thiourea (0.57 g) in a mixture of tetrahydrofuran (5 cc) and water (2 cc) is added to this reaction mixture (25 cc) containing, in solution, a mixture of the epimers of 2-benzhydryloxycarbonyl-7-t-butoxycarbonylamino-3-(1-iodo-2-oxoethyl)-8-oxo-5-thia-1-azabicyclo[4.2.0]-oct-2-ene, and the mixture is then stirred for 16 hours at 25° C. Thiourea (0.57 g) is added and the mixture is stirred for a further 3 hours at 25° C. and then diluted with ethyl acetate (150 cc). The organic phase is washed successively with distilled water (100 cc), a saturated solution of sodium bicarbonate (100 cc), distilled water (100 cc) and a semi-saturated solution of sodium chloride (100 cc). After drying over magnesium sulphate, the solvent is evaporated off under reduced pressure (30 mm Hg; 4 kPa) at 30° C. The residue is chromatographed on a column (height: 30 cm; diameter: 2 cm) of silica (0.04–0.06 mm), elution being carried out under 0.4 bar (40 kPa) with a 45/55 (by volume) mixture of cyclohexane and ethyl acetate. After evaporation of the solvents, 3-(2-aminothiazol-5-yl)-2-benzhydryloxycarbonyl-7-t-butoxycarbonylamino-8-oxo-5-thia-1-azabicyclo[4.2.0]oct-2-ene (0.08 g) is collected in the form of a hard orange foam, the characteristics of which are as follows:

Infra-red spectrum (CHBr₃), characteristic bands (cm⁻¹): 3,480, 3,420, 3,380, 1,780, 1,720, 1,600, 1,495, 1,455, 1,390, 1,370, 1,240, 1,220, 755, 740.

Proton NMR spectrum (350 MHz, CdCl₃, δ in ppm, J in Hz): 1.47 (s, 9H, —C(CH₃)₃); 3.46 and 3.61 (2d, J=18, 2H, —S—CH₂—); 5.01 (d, J=4.5, 1H, —H in the 6-position); 5.27 (b, 2H, —NH₂); 5.57 (d, J=9, 1H, —CO—NH—); 5.64 (dd, J=9 and 4.5, 1H, —H in the 7-position); 6.85 (s, 1H, —COO—CH(C₆H₅)₂); 6.94 (s, 1H, —H of the thiazole); 7.10 to 7.50 (m, 10H, aromatic protons).

EXAMPLE 10

A solution of bromine (2.69 g) in dry methylene chloride (5 cc) is added, over a period of 10 minutes, to a solution, cooled to −60° C., of the E isomer of 2-benzhydryloxycarbonyl-7-[(D)-α-t-butoxycarbonylaminophenylacetamido]-3-(2-dimethylaminovinyl)-8-oxo-5-thia-1-azabicyclo[4.2.0]oct-2-ene (11.3 g) in dry tetrahydrofuran (80 cc). The mixture is stirred for 45 minutes, the temperature being allowed to rise to −15° C., and a mixture of distilled water (0.6 cc) and tetrahydrofuran (3 cc) is then added. After 30 minutes at −15° C., a solution of thiourea (1.93 g) in a mixture of tetrahydrofuran (18 cc) and water (4 cc) is added to the reaction mixture consisting of a solution of a mixture of the epimeric bromoaldehydes of 2-benzhydryloxycarbonyl-3-(1-bromo-2-oxoethyl)-7-[(D)-α-t-butoxycarbonylaminophenylacetamido]-8-oxo-5-thia-1-azabicyclo[4.2.0]oct-2-ene. The reaction mixture is stirred for 4 hours at between 5° and 20° C. and then diluted with ethyl acetate (500 cc) and washed with a semi-saturated solution of sodium bicarbonate (300 cc), water (300 cc) and a semi-saturated solution of sodium chloride (300 cc). The residue obtained after drying of the solution over sodium sulphate and evaporation under reduced pressure (30 mm Hg) at 40° C. is chromatographed on a column (height: 30 cm; diameter: 5 cm) of silica (0.04–0.06 mm), elution being carried out under 0.4 bar (40 kPa) with a 35/65 (by volume) mixture of cyclohexane and ethyl acetate, and 100 cc fractions being collected. Fractions 18 to 31, containing the pure product, are combined and concentrated to dryness under reduced pressure (30 mm Hg; 4 kPa) at 40° C. This gives 3-(2-aminothiazol-5-yl)-2-benzhydryloxycarbonyl-7-[(D)-α-t-butoxycarbonylaminophenylacetamido]-8-oxo-5-thia-1-azabicyclo[4.2.0]oct-2-ene (2.08 g) in the form of a hard orange foam.

Infra-red spectrum (CHBr$_3$), characteristic bands (cm$^{-1}$): 3,480, 3,390, 3,200, 1,785, 1,715, 1,695, 1,600, 1,495, 1,455, 1,390, 1,370, 1,220, 760, 740.

Proton NMR spectrum (350 MHz, CDCl$_3$, δ in ppm, J in Hz): 1.43 (s, 9H, —C(CH$_3$)$_3$); 3.36 and 3.55 (2d, J=18, 2H, —S—CH$_2$—); 4.94 (s broad, 2H, —NH$_2$); 4.98 (d, J=5, 1H, —H in the 6-position);

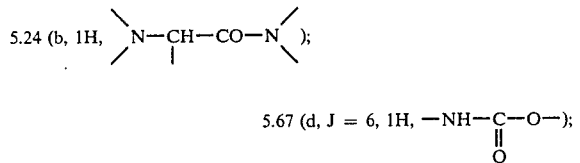

5.24 (b, 1H, \N—CH—CO—N/ );

5.67 (d, J = 6, 1H, —NH—C—O—); ‖ O 5.83 (dd, J=5 and 9, 1H, —H in the 7-position); 6.73 (b, 1H, —CO—NH—); 6.83 (s, 1H, —COO—CH(C$_6$H$_5$)$_2$); 6.94 (s, 1H, —H of the thiazole); 7.10 to 7.50 (m, 15H, aromatic protons).

EXAMPLE 11

A solution of 2-benzhydryloxycarbonyl-3-(2-dimethylaminovinyl)-8-oxo-7-phenoxyacetamido-5-thia-1-azabicyclo[4.2.0]oct-2-ene (E isomer) (14 g) in dry tetrahydrofuran (70 cc) at −55° C. is treated with a solution of bromine (1.32 cc) in dry methylene chloride (8 cc) (addition over a period of 5 minutes). The reaction mixture is stirred for 1 hour at −55° C. and then heated to −30° C. and treated with distilled water (0.9 cc). The temperature is kept at −30° C. for 2 hours and this gives a solution of a mixture of the epimeric bromoaldehydes of 2-benzhydryloxycarbonyl-3-(1-bromo-2-oxoethyl)-8-oxo-7-phenoxyacetamido-5-thia-1-azabicyclo[4.2.0]oct-2-ene, which is treated with a solution of thiourea (2.25 g) in a mixture of tetrahydrofuran (20 cc) and distilled water (6 cc). After the addition of the reagent, the reaction mixture is allowed to warm up and is stirred for 16 hours at 20° C. and then diluted with ethyl acetate (350 cc). It is washed with a saturated solution of sodium bicarbonate (300 cc) and then with distilled water (3×200 cc) and with a semi-saturated solution of sodium chloride (200 cc), dried over magnesium sulphate and filtered, and the filtrate is concentrated under reduced pressure (30 mm Hg; 4 kPa) at 30° C. The residue is chromatographed on a column (height: 50 cm; diameter: 4 cm) of silica gel (0.2–0.06 mm), elution being carried out with the following mixtures of cyclohexane and ethyl acetate; 60/40 (2 liters); 40/60 (2 liters); 30/70 (1 liter); 20/80 (1 liter) (proportions by volume), and 300 cc fractions being collected. Fractions 7 to 10, containing the pure product, are combined and evaporated to dryness under reduced pressure (30 mm Hg; 4 kPa) at 30° C. This gives 3-(2-aminothiazol-5-yl)-2-benzhydryloxycarbonyl-8-oxo-7-phenoxyacetamido-5-thia-1-azabicyclo[4.2.0]oct-2-ene (5.67 g) in the form of a hard, light yellow foam.

Infra-red spectrum (CHBr$_3$), characteristic bands (cm$^{-1}$): 3,480, 3,390, 1,780, 1,725, 1,690, 1,600, 1,455, 1,225, 750.

Proton NMR spectrum (350 MHz, CDCl$_3$, δ in ppm, J in Hz): 3.43 and 3.53 (2d, J=18, 2H, —S—CH$_2$—); 4.56 (s, 2H, —O—CH$_2$—CO—N<); 5.05 (d, J=5, 1H, —H in the 6-position); 5.22 (b, 2H, —NH$_2$); 5.87 (dd, J=9 and 5, 1H, —H in the 7-position); 6.84 (s, 1H, —COO—CH(C$_6$H$_5$)$_2$); 6.92 (s, 1H, —H of the thiazole); 6.91 (d, J=7.5, 2H, aromatic —H atoms in the ortho-positions of the phenoxy); 7.02 (t, J=7.5, 1H, aromatic —H atom in the para-position of the phenoxy); 7.15 to 7.45 (m, 12H, aromatic protons); 7.51 (d, J=9, 1H, —CO—NH—).

EXAMPLE 12

Bromine (0.043 cc) is added to a solution, cooled to −60° C., of 2-benzhydryloxycarbonyl-7-(3,4-dichlorophenylthio)-acetamido-3-(2-dimethylaminovinyl)-8-oxo-5-thia-1-azabicyclo[4.2.0]oct-2-ene (E isomer) (0.5 g) in dry tetrahydrofuran (10 cc), and the reaction mixture is stirred at −60° C. for 70 minutes and then poured into a mixture of ethyl acetate (60 cc) and distilled water (60 cc). The aqueous phase is washed with distilled water (3×60 cc) and then with a saturated solution of sodium chloride (10 cc), dried over magnesium sulphate and concentrated to dryness under reduced pressure (30 mm Hg; 4 kPa) at 30° C. to give 2-benzhydryloxycarbonyl-3-(1-bromo-2-oxoethyl)-7-(3,4-dichlorophenylthio)-acetamido-8-oxo-5-thia-1-azabicyclo[4.2.0]oct-2-ene (mixture of the two diastereoisomers at the substituent in the 3-position) (0.52 g) in the form of a hard, light beige foam.

Proton NMR spectrum (350 MHz, CDCl$_3$, δ in ppm, J in Hz): 3.32 and 3.50 (2d, J=18, 2H, 1H of each —S—CH$_2$— of the two diastereoisomers); 3.55 to 3.75 (m, 3H, 1H of each —S—CH$_2$— and —S—CH$_2$—CO—N= of the two diastereoisomers); 4.99 and 5.04 (2d, J=5, 1H, —H in the 6-position of the two diastereoisomers); 5.82 and 5.89 (2dd, J=9 and 5, 1H, —H in the 7-position of the two diastereoisomers); 5.97 and 6.01 (2s, 1H, >CHBr of the two diastereoisomers); 6.90 and 6.97 (2s, 1H, —COO—CH(C$_6$H$_5$)$_2$ of the two diastereoisomers); 7.17 and 7.18 (2dd, J=8 and 2, 1H, aromatic —H atom in the 6-position of the two diastereoisomers); 7.20 to 7.5 (m, aromatic protons);

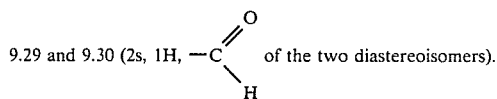

9.29 and 9.30 (2s, 1H, —C(=O)H of the two diastereoisomers).

The E isomer of 2-benzhydryloxycarbonyl-7-(3,4-dichlorophenylthio)-acetamido-3-(2-dimethylaminovinyl)-8-oxo-5-thia-1-azabicyclo[4.2.0]oct-2-ene can be obtained in the following manner:

t-Butoxy-bis-dimethylaminomethane (2.17 cc) is added to a solution of 2-benzhydryloxycarbonyl-7-(3,4-dichlorophenylthio)-acetamido-3-methyl-8-oxo-5-thia-1-azabicyclo[4.2.0]oct-2-ene (4.2 g) in dry, N,N-dimethylformamide (40 cc) at 80° C., and the reaction mixture is then stirred for 15 minutes at 80° C. before being poured into a mixture of ethyl acetate (500 cc) and distilled water (150 cc). The organic phase is washed with distilled water (3×150 cc) and then with a saturated solution of sodium chloride (50 cc). The residue obtained after concentration to dryness under reduced pressure (30 mm Hg; 4 kPa) at 40° C. is chromatographed on a column (height: 32 cm, diameter: 6 cm) of silica gel (0.04–0.063 mm), elution being carried out under a pressure of 0.5 bar (50 kPa) with a mixture of cyclohexane and ethyl acetate (40/60 by volume), and 100 cc fractions being collected. Fractions 10 to 14 are combined and concentrated to dryness under reduced pressure (30 mm Hg; 4 kPa) at 30° C. to give the E isomer of 2-benzhydryloxycarbonyl-7-(3,4-dichlorophenylthio)acetamido-3-(2-dimethylaminovinyl)-8-oxo-5-thia-1-azabicyclo[4.2.0]oct-2-ene (0.51 g) in the form of a hard yellow foam.

Proton NMR spectrum (250 MHz, CDCl$_3$, δ in ppm, J in Hz): 2.79 and 3.08 (2d, J=15, 2H, —S—CH$_2$—); 2.85 (s, 6H, —N(CH$_3$)$_2$); 3.76 (s, 2H, —CH$_2$—CO—N=); 5.07 (d, J=4.5, 1H, —H in the 6-position); 5.4 (dd, J=8 and 4.5, 1H, —H in the 7-position); 6.34 and 6.48 (2d, J=13.5, 2H, —CH=CH—); 6.82 (s, 1H, —COO—CH(C$_6$H$_5$)$_2$); 7.15 to 7.55 (m, aromatic protons); 8.0 (d, $\bar{J}$=8, 1H, —CO—NH—).

2-Benzhydryloxycarbonyl-7-(3,4-dichlorophenylthio)acetamido-3-methyl-8-oxo-5-thia-1-azabicyclo[4.2.0]oct-2-ene can be prepared by reacting 3,4-dichlorophenylthioacetyl chloride with 7-amino-2-benzhydryloxycarbonyl-3-methyl-8-oxo-5-thia-1-azabicyclo[4.2.0]oct-2-ene.

Proton NMR spectrum (250 MHz, CDCl$_3$, δ in ppm, J in Hz): 2.09 (s, 3H, —CH$_3$); 3.13 and 3.40 (2d, J=18, 2H, —SCH$_2$—); 3.60 and 3.71 (2d, J=16, 2H, —SCH$_2$CO—); 4.92 (d, J=5, 1H in the 6-position); 5.74 (dd, J=5 and 9, 1H, H in the 7-position); 6.94 (s, 1H, —COOCH<); 7.16 (dd, J=2 and 8.5, H in the 6-position of the phenyl); 7.20 to 7.45 (b, 13H, benzhydryl+—CONH—+H in the 5-position and in the 2-position of the phenyl).

EXAMPLE 13

A solution of 85% pure meta-chloroperbenzoic acid (4.31 g) in methylene chloride (50 cc) is added dropwise, over a period of 30 minutes, to a solution, cooled to between 0° and −5° C., of 2-benzhydryloxycarbonyl-3-(1-bromo-2-oxoethyl)-7-t-butoxycarbonylamino-8-oxo-5-thia-1-azabicyclo[4.2.0]oct-2-ene (mixture of the diastereoisomers at the substituent in the 3-position) (14.69 g) in methylene chloride (150 cc). After 30 minutes at −5° C., the reaction mixture is poured into a mixture of a semi-saturated solution of sodium bicarbonate (100 cc) and methylene chloride (200 cc). The organic phase is washed with distilled water (150 cc) and a semi-saturated solution of sodium chloride (150 cc) and then dried over sodium sulphate and concentrated to dryness under reduced pressure (30 mm Hg; 4 kPa) at 20° C. to give crude 2-benzhydryloxycarbonyl-3-(1-bromo-2-oxoethyl)-7-t-butoxycarbonylamino-8-oxo-5-thia-1-azabicyclo[4.2.0]oct-2-ene-5-oxide (mixture of the diastereoisomers at the substituent in the 3-position) (13.35 g) in the form of a hard, light brown foam. The crude product obtained is divided into 2 batches, which are chromatographed on a column (height: 30 cm, diameter: 5 cm) of silica gel (0.04–0.063 mm), elution being carried out under a pressure of 0.4 bar (40 kPa) with a mixture of cyclohexane and ethyl acetate (40/60 by volume), and 125 cc fractions being collected. Fractions 7 to 10 from both chromatographic separations are combined and concentrated to dryness under reduced pressure (30 mm HG; 4 kPa) at 20° C. to give 2-benzhydryloxycarbonyl-3-(1-bromo-2-oxoethyl)-7-t-butoxycarbonylamino-8-oxo-5-thia-1-azabicyclo[4.2.0]oct-2-ene-5-oxide (mixture of the diastereoisomers at the substituent in the 3-position) (2.43 g) in the form of a hard yellow foam.

Infra-red spectrum (CHCl$_3$), characteristic bands (cm$^{-1}$): 3,420, 1,805, 1,720, 1,505, 1,453, 1,395, 1,370, 1,160, 1,050.

Proton NMR spectrum (350 MHz, CDCl$_3$, δ in ppm, J in Hz): 1.47 (s, 9H, —C(CH$_3$)$_3$ of the two diastereoisomers); 3.27 and 3.42 (2d, J=18, 2H, 1H of —SCH$_2$— of each of the two diastereoisomers); 3.83 and 3.98 (2d, J=18, 2H, 1H of —SCH$_2$— of each of the two diastereoisomers); 4.50 and 4.60 (2d, J=4, 1H, —H in the 6-position of the two diastereoisomers); 5.70 to 5.97 (m, 2H, —H in the 7-position and —CONH— of the two diastereoisomers); 6.25 and 6.29 (2s, 1H, >CHBr of the two diastereoisomers); 6.94 and 6.98 (2s, 1H, —COO—CH(C$_6$H$_5$)$_2$ of the two diastereoisomers); 7.20 to 7.50 (m, aromatic protons of the two diastereoisomers);

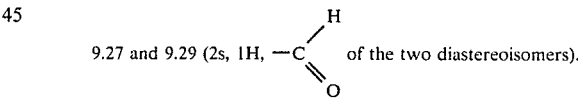

9.27 and 9.29 (2s, 1H, —C(H)=O of the two diastereoisomers).

EXAMPLE 14

By oxidising 2-benzhydryloxycarbonyl-7-t-butoxycarbonylamino-3-(1-chloro-2-oxoethyl)8-oxo-5-thia-1-azabicyclo[4.2.0]oct-2-ene (mixture of the diastereoisomers) (53 g) with 90% pure m-chloroperbenzoic acid (19 g) in methylene chloride (700 cc), following the procedure of Example 13, crude 2-benzhydryloxycarbonyl-7-t-butoxycarbonylamino-3-(1-chloro-2-oxoethyl)-8-oxo-5-thia-1-azabicyclo[4.2.0]oct-2-ene-5-oxide (mixture of the diastereoisomers) (44.8 g) is obtained in the form of a hard brown foam.

Rf=0.24–0.4 (silica gel chromatography plate, eluted with a mixture of cyclohexane and ethyl acetate, 35/65 by volume).

REFERENCE EXAMPLE 1

The product of Example 1 can be used in the following manner:

A solution of acetylthiourea (1.8 g) in dry tetrahydrofuran (20 cc) is added, over a period of 5 minutes, to a solution, cooled to 3° C., of a mixture of the epimers of 2-benzhydryloxycarbonyl-7-t-butoxycarbonylamino-3-(1-bromo-2-oxoethyl)-8-oxo-5-thia-1-azabicyclo[4.2.0]oct-2-ene (5.87 g) in dry tetrahydrofuran (58.7 cc). The reaction mixture is then stirred for 4 hours 30 minutes at 25° C. and then diluted with ethyl acetate (150 cc) and a saturated solution of sodium bicarbonate (150 cc). The organic layer is washed with distilled water (2×100 cc) and then with a saturated solution of sodium chloride (100 cc) and dried. After evaporation of the solvent under reduced pressure (30 mm Hg; 4 kPa) at 30° C., the residue is chromatographed on a column (height: 30 cm; diameter: 6 cm) of silica (0.04–0.06 mm), elution being carried out under a pressure of 0.4 bar (40 kPa) with a 70/30 (by volume) mixture of cyclohexane and ethyl acetate (1,600 cc) and then with a 30/70 (by volume) mixture of cyclohexane and ethyl acetate (2,000 cc), and 100 cc fractions being collected. Fractions 27 to 33, containing the pure product, are combined and concentrated to dryness. This gives 3-(2-acetamidothiazole-5-yl)-2-benzhydryloxycarbonyl-7-t-butoxycarbonylamino-8-oxo-5-thia-1-azabicyclo[4.2.0]oct-2-ene (0.54 g) in the form of a hard yellow foam.

Rf=0.45; silica gel chromatography plate, eluant: cyclohexane/ethyl acetate, 25/75 (by volume).

Infra-red spectrum (CHBr$_3$), characteristic bands (cm$^{-1}$): 3,400, 3,270, 3,220, 3,180, 1,790, 1,730, 1,700, 1,545, 1,510, 1,495, 1,455, 1,370, 1,230, 1,165, 760, 745, 700.

Proton NMR spectrum (350 MHz, d$_6$-DMSO, δ in ppm, J in Hz): 1.42 (s, 9H, (CH$_3$)$_3$C—); 2.41 (s, 3H, CH$_3$CO—); 3.76 and 3.88 (AB system, J=18, 2H, —SCH$_2$—); 5.17 (d, J=4, 1H, H in the 6-position); 5.59 (dd, J=4 and 9, 1H, H in the 7-position); 6.81 (s, 1H, —CHAr$_2$); 7 to 7.4 (m, 11H, H$_4$ of the thiazole and aromatic protons); 8.04 (d, J=9, 1H, —CONH—C$_7$); 12.05 (s, 1H, —N$\underline{H}$—COCH$_3$).

3-(2-Acetamidothiazol-5-yl)-2-benzhydryloxycarbonyl-7-t-butoxycarbonylamino-8-oxo-5-thia-1-azabicyclo[4.2.0]oct-2-ene (4.6 g) is dissolved in acetonitrile (190 cc) at 35° C. and treated with a solution of p-toluenesulphonic acid (monohydrate) (2.9 g) in acetonitrile (20 cc) for 3 hours at 35° C., for 16 hours at 25° C. and then for a further 6 hours at 35° C. after the addition of p-toluenesulphonic acid (monohydrate) (0.95 g). The reaction mixture is partially concentrated under reduced pressure (30 mm Hg; 4 kPa) at 30° C. and then diluted with methylene chloride (200 cc) and a saturated solution of sodium bicarbonate (200 cc). The aqueous layer is extracted with methylene chloride (100 cc) and the combined organic solutions are washed with water (200 cc) and then dried and concentrated under reduced pressure (30 mm Hg; 4 kPa) at 30° C. The residue is dried under reduced pressure (10 mm Hg; 1.3 kPa) at 25° C. This gives crude 3-(2-acetamidothiazol-5-yl)-7-amino-2-benzhydryloxycarbonyl-8-oxo-5-thia-1-azabicyclo[4.2.0]oct-2-ene (3.3 g) in the form of a beige powder.

Infra-red spectrum (CHBr$_3$), characteristic bands (cm$^{-1}$): 3,440, 3,400, 3,340, 3,260, 3,160, 1,780, 1,720, 1,695, 1,670, 1,560, 1,515, 1,495, 1,450, 1,370, 1,220, 760.

Proton NMR spectrum (350 MHz, CDCl$_3$, δ in ppm, J in Hz): 2.15 (s, 3H, —CO—CH$_3$); 3.57 and 3.74 (2d, J=18, 2H, —S—CH$_2$); 4.84 (d, J=4.5, 1H, —H in the 7-position); 5.05 (d, J=4.5, 1H, —H in the 6-position); 6.92 (s, 1H, —COO—C$\underline{H}$(C$_6$H$_5$)$_2$); 7.03 (s, 1H, —H of the thiazole); 7.05 to 7.50 (m, aromatic protons); 11.45 (b, 1H, —NH—CO—).

A solution of (thien-2-yl)-acetyl chloride (0.55 cc) in dry tetrahydrofuran (5 cc) is added, over a period of 5 minutes, to a solution of 3-(2-acetamidothiazol-5-yl)-7-amino-2-benzhydryloxycarbonyl-8-oxo-5-thia-1-azabicyclo[4.2.0]oct-2-ene (2.27 g) in dry tetrahydrofuran (27.5 cc) at 2° C., and a solution of triethylamine (0.63 cc) in dry tetrahydrofuran (5 cc) is then added after 30 minutes. After a reaction time of 1 hour at 2° C., the reaction mixture is filtered and the filtrate is diluted in a mixture of ethyl acetate (200 cc) and a semi-saturated solution of sodium bicarbonate (200 cc). The organic layer is washed with water (100 cc) and then with a saturated solution of sodium chloride (100 cc), dried over magnesium sulphate and concentrated to dryness under reduced pressure (30 mm Hg; 4 kPa) at 40° C. The residue is chromatographed on a column (height: 30 cm; diameter: 5 cm) of silica (0.04–0.06 mm), elution being carried out under 0.4 bar (40 kPa) with a 30/70 (by volume) mixture of cyclohexane and ethyl acetate, and 50 cc fractions being collected. Fractions 15 to 22, containing the pure product, are combined and concentrated under reduced pressure (30 mm Hg; 4 kPa) at 40° C. This gives 3-(2-acetamidothiazol-5-yl)-2-benzhydryloxycarbonyl-8-oxo-7-(thien-2-yl-acetamido)-5-thia-1-azabicyclo[4.2.0]oct-2-ene (0.92 g) in the form of a yellow powder.

Infra-red spectrum (KBr), characteristic bands (cm$^{-1}$): 3,280, 3,200, 2,500, 1,785, 1,770, 1,725, 1,695, 1,670, 1,650, 1,550, 1,530, 1,495, 1,450, 1,220, 690.

Proton NMR spectrum (350 MHz, CDCl$_3$, δ in ppm, J in Hz): 2.09 (s, 3H, CH$_3$CO—); 3.47 (limiting AB system, 2H, —SCH$_2$—); 3.84 (s, 2H, ArCH$_2$CO—); 5.04 (d, J=4.5, 1H, H in the 6-position); 5.88 (dd, J=4.5 and 9, 1H, H in the 7-position); 6.83 (s, 1H, —OCe,uns/H/Ar$_2$); 6.9 to 7.0 (m, 2H, H in the 3-position and 4-position of the thiophene); 7.13 (s, 1H, H in the 4-position of the thiazole); 7.10 to 7.45 (m, 16H, aromatic protons, H in the 5-position of the thiophene and —CONH-C$_7$).

A solution of 3-(2-acetamidothiazol-5-yl)-2-benzhydryloxycarbonyl-8-oxo-7-(thien-2-yl-acetamido)-5-thia-1-azabicyclo[4.2.0]oct-2-ene (0.85 g) in formic acid (20 cc) is stirred for 30 minutes at 50° C. and then concentrated to dryness under reduced pressure (10 mm Hg; 1.3 kPa) at 40° C. The residue is taken up in ethanol (50 cc), the mixture is stirred for 5 minutes at 50° C. and the solvent is then evaporated off to dryness under reduced pressure (30 mm Hg; 4 kPa) at 40° C. The residue is taken up in ethanol (100 cc); the mixture is stirred for 10 minutes at 50° C. and the solid is then filtered off and washed with ethanol (3×15 cc) and ethyl ether (3×10 cc). After drying, 3-(2-acetamidothiazol-5-yl)-2-carboxy-8-oxo-7-(thien-2-yl-acetamido)-5-thia-1-azabicyclo[4.2.0]oct-2-ene (0.53 g) is obtained in the form of a light yellow powder.

Infra-red spectrum (KBr), characteristic bands (cm$^{-1}$): 3,260, 3,200, 3,100 to 2,200, 1,780, 1,685, 1,650, 1,545, 1,370, 700.

Proton NMR spectrum (350 MHz, d$_6$-DMSO, δ in ppm, J in Hz): 2.15 (s, 3H, —CO—CH$_3$); 3.74 and 3.80 (2d, J=14, 2H, —CO—CH$_2$—); 3.76 and 3.88 (2d, J=18, 2H, —CH$_2$—S—); 5.16 (d, J=5, 1H, —H in the 6-position); 5.72 (dd, J=5 and 9, 1H, —H in the 7-position); 6.90 to 7 (m, 2H, =CH—CH= of the thiophene); 7.35 (dd, J=4 and 1, 1H, =CH—S— of the thiophene); 7.50 (s, 1H, —H of the thiazole); 9.16 (d, J=9, 1H, —CO—NH—); 13.13 (s broad, 1H, —N$\underline{H}$—CO—CH$_3$).

REFERENCE EXAMPLE 2

3-(2-Acetamidothiazol-5-yl)-7-amino-2-benzhydryloxycarbonyl-8-oxo-5-thia-1-azabicyclo[4.2.0]oct-2-ene (obtained as described in Reference Example 1) (3.4 g) is acylated with (1,3-dithiol-2-on-4-yl)-acetyl chloride (1.95 g) in dry tetrahydrofuran (75 cc), in the presence of triethylamine (1.4 cc), by following the procedure described in Reference Example 1. The crude product is chromatographed on a column (height: 30 cm; diameter: 6 cm) of silica gel (0.04–0.06 mm), elution being carried out under a pressure of 0.4 bar (40 kPa) with a 20/80 (by volume) mixture of cyclohexane and ethyl acetate, and 100 cc fractions being collected. Fractions 11 to 20 are combined and concentrated to dryness under reduced pressure (30 mm Hg; 4 kPa) at 30° C. This gives the expected product (1.87 g), which is crystallised from acetonitrile (90 cc). This gives 3-(2-acetamidothiazol-5-yl)-2-benzhydryloxycarbonyl-7-(1,3-dithiol-2-on-4-yl-acetamido)-8-oxo-5-thia-1-azabicyclo[4.2.0]oct-2-ene (0.8 g) in the form of white crystals.

Infra-red spectrum (KBr), characteristic bands (cm$^{-1}$): 3,280, 1,780, 1,730, 1,695, 1,640, 1,545, 1,225, 700.

Proton NMR spectrum (350 MHz, d$_6$-DMSO, δ in ppm, J in Hz): 2.14 (s, 3H, —CO—CH$_3$); 3.67 (s, 2H, —CH$_2$—CO—N<); 3.79 and 3.92 (2d, J=18, 2H, —CH$_2$—S—); 5.23 (d, J=4.5, 1H, —H in the 6-position); 5.8 (dd, J=4.5 and 9, 1H, —H in the 7-position); 6.83 (s, 1H, —COOCH(C$_6$H$_5$)$_2$); 7.01 (s, 1H, —S—CH=); 7.03 to 7.4 (m, 11H, aromatic protons and —H of the thiazole); 9.3 (d, J=9, 1H, —CO—NH—); 12.06 (s, 1H, —NH—CO—CH$_3$).

By following the procedure described in Reference Example 1, but starting from 3-(2-acetamidothiazol-5-yl)-2-benzhydryloxycarbonyl-7-(1,3-dithiol-2-on-4-yl-acetamido)-8-oxo-5-thia-1-azabicyclo[4.2.0]oct- 2-ene (0.8 g), 3-(2-acetamidothiazol-5-yl)-2-carboxy-7-(1,3-dithiol-2-on-4-yl-acetamido)-8-oxo-5-thia-1-azabicyclo[4.2.0]oct-2-ene (0.2 g) is obtained in the form of a beige solid.

Infra-red spectrum (KBr), characteristic bands (cm$^{-1}$): 3,270, 3,100 to 2,100, 1,785, 1,685, 1,640, 1,545.

Proton NMR spectrum (350 MHz, d$_6$-DMSO, δ in ppm, J in Hz): 2.14 (s, 3H, —CO—CH$_3$); 3.65 (s, 2H, —CH$_2$—CO—N<); 3.77 and 3.91 (2d, J=18, 2H, —CH$_2$—S—); 5.18 (d, J=5, 1H, —H in the 6-position); 5.68 (dd, J=5 and 9, 1H, —H in the 7-position); 7.01 (s, 1H, —S—CH=); 7.52 (s, 1H, H of the thiazole); 9.27 (d, J=9, 1H, —CO—NH—); 12.15 (s broad, 1H, —NH—CO—CH$_3$).

REFERENCE EXAMPLE 3

The product of Example 1 can be used in the following manner:

A solution of 2-benzhydryloxycarbonyl-3-(1-bromo-2-oxoethyl)-7-t-butoxycarbonylamino-8-oxo-5-thia-1-azabicyclo[4.2.0]oct-2-ene (mixture of the epimers of the bromoaldehyde) (5.87 g) and thiobenzamide (1.5 g) in dry tetrahydrofuran (60 cc) is stirred at 20° C. for 1 hour 20 minutes, methanesulphonyl chloride (0.85 cc) is then added to the reaction mixture, cooled to 2° C., and triethylamine (5.6 cc) is then added over a period of 5 minutes. After stirring for 2 hours at 2° C., the reaction mixture is poured into a mixture of ethyl acetate (100 cc) and 1 N hydrochloric acid (50 cc). The organic phase is washed with a saturated solution of sodium bicarbonate (100 cc) and then with a saturated solution of sodium chloride (100 cc), dried over magnesium sulphate and concentrated to dryness under reduced pressure (30 mm Hg; 4 kPa) at 30° C. The residue is chromatographed on a column (height: 25 cm; diameter: 5 cm) of silica gel (0.04–0.06 mm), elution being carried out under a pressure of 0.4 bar (40 kPa) with an 80/20 (by volume) mixture of cyclohexane and ethyl acetate, and 125 cc fractions being collected. Fractions 17 to 22, containing the pure product, are combined and concentrated to dryness under reduced pressure (30 mm Hg; 4 kPa) at 30° C. This gives 2-benzhydryloxycarbonyl-7-t-butoxycarbonylamino-8-oxo-3-(2-phenylthiazol-5-yl)-5-thia-1-azabicyclo[4.2.0]oct-2-ene (1 g) in the form of a hard yellow foam.

Infra-red spectrum (CHBr$_3$), characteristic bands (cm$^{-1}$): 3,420, 1,790, 1,720, 1,595, 1,495, 1,450, 1,500, 1,420, 1,390, 1,370, 1,235, 760, 740.

Proton NMR spectrum (350 MHz, CDCl$_3$, δ in ppm, J in Hz): 1.48 (s, 9H, —C(CH$_3$)$_3$); 3.62 and 3.78 (2d, J=18, 2H, —CH$_2$—S—); 5.10 (d, J=5, 1H, —H in the 6-position); 5.29 (d, J=9, 1H, —CO—NH—); 5.73 (dd, J=5 and 9, 1H, —H in the 7-position); 6.96 (s, 1H, —COOCH(C$_6$H$_5$)$_2$); 7 to 7.5 (m, aromatic protons); 7.54 (s, 1H, —H of the thiazole); 7.77 (m, 2H, aromatic —H atoms of the phenyl in the ortho-positions to the thiazole).

2-Benzhydryloxycarbonyl-7-t-butoxycarbonylamino-8-oxo-3-(2-phenylthiazol-5-yl)-5-thia-1-azabicyclo[4.2.0]oct-2-ene (5.7 g) is treated with trifluoroacetic acid (57 cc) for 20 minutes at 20° C. and the reaction mixture is then concentrated to dryness under reduced pressure (0.2 mm Hg; 0.03 kPa) at 30° C. The residue is taken up in ethyl acetate (100 cc), which is evaporated off under reduced pressure (30 mm Hg; 4 kPa) at 30° C. The residue is triturated in isopropyl ether (100 cc). The solid is filtered off, washed with isopropyl ether (3×50 cc) and dried under reduced pressure (0.2 mm Hg; 0.03 kPa) at 20° C. This gives 7-amino-2-carboxy-8-oxo-3-(2-phenylthiazol-5-yl)-5-thia-1-azabicyclo[4.2.0]oct-2-ene (3.3 g) in the form of an ochre solid.

Infra-red spectrum (KBr), characteristic bands (cm$^{-1}$): 3,300 to 2,000, 1,785, 1,615, 1,400, 760, 690.

Proton NMR spectrum (350 MHz, d$_6$-DMSO, δ in ppm, J in Hz): 3.82 and 3.92 (d, J=18, 2H, —S—CH$_2$—); 4.92 (d, J=4.5, 1H, —H in the 7-position); 5.13 (d, J=4.5, 1H, —H in the 6-position); 7.40 to 7.60 (m, aromatic —H atoms of the benzene in the meta-positions and in the para-position to the thiazole); 7.85 to 8 (m, aromatic —H atoms of the benzene in the ortho-positions to the thiazole, and —H of the thiazole).

A solution of 7-amino-2-carboxy-8-oxo-3-(2-phenylthiazol-5-yl)-5-thia-1-azabicyclo[4.2.0]oct-2-ene (3.3 g) in a mixuture of distilled water (35 cc) and acetone (24 cc), containing sodium bicarbonate (2 g), is cooled to =10° C. and then treated with a solution of (thien-2-yl)-acetyl chloride (0.86 cc) in acetone (10 cc), which is added dropwise over a period of 8 minutes. The reaction mixture is stirred for 30 minutes at −10° C. and then for 3 hours at 20° C. The acetone is evaporated off under reduced pressure (30 mm Hg; 4 kPa) at 30° C. and ethyl acetate (150 cc) and a saturated solution of sodium bicarbonate (100 cc) are added. The aqueous layer is extracted with ethyl acetate (100 cc) and then treated with decolorising charcoal (1 g) and a filter aid (diatomaceous earth) (5 g) and filtered on a filter aid, the material on the filter being rinsed with distilled water (2×50 cc). The combined filtrates are acidified to pH=2 with 4 N hydrochloric acid. The precipitate is filtered off, washed with ethyl acetate (50 cc) and then triturated in isopropyl ether (100 cc) and dried. This gives 2-carboxy-8-oxo-3-(2-phenylthiazol-5-yl)-7-(thien-2-yl-acetamido)-5-thia-1-azabicyclo[4.2.0]oct-2-ene (0.8 g) in the form of a cream-coloured solid.

Infra-red spectrum (KBr), characteristic bands (cm$^{-1}$): 3,290, 2,700–2,200, 1,780, 1,730, 1,690, 1,530, 1,450, 690.

Proton NMR spectrum (350 MHz, d$_6$-DMSO, δ in ppm, J in Hz): 3.74 and 3.82 (2d, J=14, 2H, —CH$_2$—CO—N<); 3.86 and 3.96 (2d, J=18, 2H, —S—CH$_2$—); 5.23 (d, J=4.5, 1H, —H in the 6-position); 5.77 (dd, J=4.5 and 9, 1H, —H in the 7-position); 6.90 to 7 (m, 2H, =CH—CH= of the thiophene); 7.35 (dd, J=4.5 and 1, 1H, =CH—S— of the thiophene); 7.45 to 7.55 (m, 3H, aromatic —H atoms of the benzene in the meta-positions and in the para-position to the thiazole); 7.92 (d, J=8, 2H, aromatic —H atoms of the benzene in the ortho-positions to the thiazole); 7.93 (s, 1H, —H of the thiazole); 9.21 (d, J=9, 1H, —CONH—).

2-Carboxy-8-oxo-3-(2-phenylthiazol-5-yl)-7-(thien-2-yl-acetamido)-5-thia-1-azabicyclo[4.2.0]oct-2-ene (0.336 g) is dissolved in a solution of sodium bicarbonate (0.05 g) in water (10 cc). After washing with ethyl acetate (25 cc), the aqueous phase is filtered and the filtrate is then lyophilised. This gives the sodium salt of 2-carboxy-8-oxo-3-(2-phenylthiazol-5-yl)-7-(thien-2-yl-acetamido)-5-thia-1-azabicyclo[4.2.0]oct-2-ene (0.32 g) in the form of a beige lyophilisate.

Infra-red spectrum (KBr), characteristic bands (cm$^{-1}$): 3,280, 1,760, 1,665, 1,605, 1,545, 1,495, 1,450, 1,395, 690.

Proton NMR spectrum (d$_6$-DMSO, δ in ppm, J in Hz): 3.68 and 3.81 (2d, J=16, 2H, —SCH$_2$—); 3.77 (s, 2H, —CH$_2$CO—); 5.08 (d, J=5, 1H, H in the 6-position); 5.54 (dd, J=5 and 8, 1H, H in the 7-position); 6.9 to 7 (m, 2H, H$_3$ and H$_4$ of the thienyl); 7.36 (dd, J=1 and 5, 1H, H$_5$ of the thienyl); 7.4 to 7.5 (m, 3H, H$_3$, H$_4$ and H$_5$ of the phenyl); 7.85 (d, J=7.5, 2H, H$_2$ and H$_6$ of the phenyl); 7.90 (s, 1H, H in the 4-position of the thiazole); 9.15 (d, J=9, 1H, —CONH—).

REFERENCE EXAMPLE 4

The product of Example 1 can be used in the following manner:

A solution of 2-benzhydryloxycarbonyl-3-(1-bromo-2-oxoethyl)-7-t-butoxycarbonylamino-8-oxo-5-thia-1-azabicyclo[4.2.0]oct-2-ene (mixture of the epimeric bromoaldehydes) (2.34 g) and thioformamide (0.3 g) in dry tetrahydrofuran (23 cc) is stirred for 3 hours at 20° and then heated for 90 minutes at 50° C. The reaction mixture is diluted with ethyl acetate (160 cc) and washed with a saturated solution of sodium bicarbonate (100 cc) and then with a semi-saturated solution of sodium chloride (100 cc). After drying of the organic layer over magnesium sulphate and evaporation of the solvent under reduced pressure (30 mm Hg; 4 kPa) at 30° C., the residue obtained is subjected to chromatography on a column (height: 30 cm; diameter: 2.5 cm) of silica gel (0.04–0.06 mm), elution being carried out under a pressure of 0.8 bar (80 kPa) with a 70/30 (by volume) mixture of cyclohexane and ethyl acetate, and 50 cc fractions being collected. Fractions 16 to 25, containing the pure product, are combined and concentrated to dryness under reduced pressure (30 mm Hg; 4 kPa) at 30° C., and the residue is triturated in isopropyl ether (50 cc). After filtration and drying, 2-benzhydryloxycarbonyl-7-t-butoxycarbonylamino-8-oxo-3-(thiazol-5-yl)-5-thia-1-azabicyclo[4.2.0]oct-2-ene (0.85 g) is obtained in the form of a cream-coloured solid.

Infra-red spectrum (CHBr$_3$), characteristic bands (cm$^{-1}$): 3,420, 1,790, 1,725, 1,505, 1,500, 1,455, 1,390, 1,370, 870, 760, 740.

Proton NMR spectrum (350 MHz, CDCl$_3$, δ in ppm, J in Hz): 1.49 (s, 9H, —C(CH$_3$)$_3$); 3.56 and 3.74 (2d, J=18, 2H, —S—CH$_2$—); 5.09 (d, J=4.5, 1H, —H in the 6-position); 5.32 (d, J=9, 1H, —CO—NH—); 5.72 (dd, J=9 and 4.5, 1H, —H in the 7-position); 6.91 (s, 1H, —COOCH(C$_6$H$_5$)$_2$); 7 to 7.4 (m, 10H, aromatic protons); 7.85 (s, 1H, H of the thiazole); 8.58 (s, 1H, H$_2$ of the thiazole).

By following the procedure described in Reference Example 1, starting from 2-benzhydryloxycarbonyl-7-t-butoxycarbonylamino-8-oxo-3-(thiazol-5-yl)-5-thia-1-azabicyclo[4.2.0]oct-2-ene (3.85 g), the 7-amino derivative is prepared by reaction with methanesulphonic acid (3.8 cc) in acetonitrile (38 cc), and the crude 7-amino-2-benzhydryloxycarbonyl-8-oxo-3-(thiazol-5-yl)-5-thia-1-azabicyclo[4.2.0]oct-2-ene obtained is then acylated with (thien-2-yl)-acetyl chloride (0.86 cc) in dry tetrahydrofuran (65 cc), in the presence of triethylamine (0.98 cc). After chromatography on a column (height: 30 cm; diameter=4 cm) of silica gel (0.04–0.06 mm), elution being carried out under a pressure of 0.4 bar (40 kPa) with a 30/70 (by volume) mixture of cyclohexane and ethyl acetate, and concentration to dryness, under reduced pressure, of fractions 11 to 20 (each of 40 cc), containing the pure product, 2-benzhydryloxycarbonyl-8-oxo-3-(thiazol-5-yl)-7-(thien-2-yl-acetamido)-5-thia-1-azabicyclo[4.2.0]oct-2-ene (2.67 g) is obtained in the form of a hard cream-coloured foam.

Infra-red spectrum (CHCl$_3$), characteristic bands (cm$^{-1}$): 3,400, 1,790, 1,730, 1,690, 1,505, 695.

Proton NMR spectrum (350 MHz, CDCl$_3$, δ in ppm, J in Hz): 3.51 and 3.71 (2d, J=18, 2H, —S—CH$_2$—); 3.88 (s, 2H, —CH$_2$C0—N<); 5.09 (d, J=5, 1H, —H in the 6-position); 5.94 (dd, J=5 and 9, 1H, —H in the 7-position); 6.43 (d, J=9, 1H, —CO—NH—); 6.90 (s, 1H, —COOCH (C$_6$H$_5$)$_2$); 6.98 to 7.05 (m, H$_3$ and H$_4$ of the thiophene); 7.05 to 7.45 (m, 11H, aromatic protons and H$_5$ of the thiophene); 7.55 (s, 1H, H$_4$ of the thiazole); 8.59 (s, 1H, H$_2$ of the thiazole).

By following the procedure described in Reference Example 1, but starting from 2-benzhydryloxycarbonyl-8-oxo-3-(thiazol-5-yl)-7-(thien-2-yl-acetamido)-5-thia-1-azabicyclo[4.2.0]oct -2-ene (2.55 g), 2-carboxy-8-oxo-3-(thiazol-5-yl)-7-(thien-2-yl-acetamido)-5-thia-1-azabicyclo[4.2.0]oct -2-ene (1.03 g) is obtained in the form of a beige solid.

Infra-red spectrum (KBr), characteristic bands (cm$^{-1}$): 3,260, 3,150–2,200, 1,780, 1,655, 1,540, 1,220, 700.

Proton NMR spectrum (350 MHz, d$_6$-DMSO, δ in ppm, J in Hz): 3.80 and 3.87 (2 limiting AB systems, 4H, —CH$_2$—CO—N< and —CH$_2$—S—); 5.20 (d, J=4.5, 1H, —H in the 6-position); 5.76 (dd, J=9 and 4.5, 1H, —H in the 7-position); 6.90 to 7 (m, 2H, H$_3$ and H$_4$ of the thiophene); 7.35 (dd, J=5 and 1, 1H, H in the 5-position of the thiophene); 7.91 (s, 1H, H$_4$ of the thiazole); 9.09 (s, 1H, H in the 2-position of the thiazole); 9.19 (d, J=9, 1H, —CO—NH—); 13.65 (b, 1H, —COOH).

REFERENCE EXAMPLE 5

Following the procedure described in Reference Example 3, 2-benzhydryloxycarbonyl-7-t-butoxycarbonylamino-8-oxo-3-(thiazol-5-yl)-5-thia-1-azabicyclo[4.2.0]oct-2-ene (obtained as described in Reference Example 4) (5.2 g) is treated with trifluoroacetic acid (80 cc). This gives 7-amino-2-carboxy-8-oxo-3-(thiazol-5-yl)-5-thia-1-azabicyclo[4.2.0]oct-2-ene trifluoroacetate (4 g) in the form of a cream-coloured solid.

Infra-red spectrum (KBr), characteristic bands (cm$^{-1}$): 3,300–2,200, 1,785, 1,680, 1,620, 1,205, 1,180, 1,140, 800, 725.

Isobutyl chloroformate (1.3 cc) is added to a suspension, cooled to $-10°$ C., of (D)-N-t-butoxycarbonyl-(4-hydroxyphenyl)-glycine (2.53 g) and triethylamine (1.33 cc) in tetrahydrofuran (40 cc), and the reaction mixture is then stirred at a temperature of between $-10°$ and $-15°$ C. for 1 hour before adding a solution of 7-amino-2-carboxy-8-oxo-3-(thiazol-5-yl)-5-thia-1-azabicyclo[4.2.0]oct-2-ene trifluoroacetate (3.8 g) and triethylamine (4 cc) in a mixture of tetrahydrofuran (20 cc) and distilled water (20 cc) over a period of 10 minutes. The reaction mixture is stirred for 1 hour at a temperature of between 0° and 5° C. and then for 2 hours at 20° C. After evaporation of the tetrahydrofuran under reduced pressure (30 mm Hg; 4 kPa) at 30° C., a saturated solution of sodium bicarbonate (50 cc) is added and the aqueous phase is washed with ethyl acetate (100 cc) before being acidified to pH 2 with 4 N hydrochloric acid and then being extracted with ethyl acetate (2×100 cc). The organic phase is washed with distilled water (100 cc) and with a saturated solution of sodium chloride (100 cc) and then dried and concentrated to dryness under reduced pressure (30 mm Hg; 4 kPa) at 30° C. This gives crude 7-[(D)-α-t-butoxycarbonylamino-(4-hydroxyphenyl)-acetamido]-2-carboxy-8-oxo-3-(thiazol-5-yl)-5-thia-1-azabicyclo[4.2.0]oct-2-ene (1.2 g) in the form of a hard yellow foam [Rf=0.35; silica gel chromatography plate, eluant: mixture of ethyl acetate, acetone, water and formic acid (50/10/5/5 by volume)], which is purified by conversion to its benzhydryl ester in the following manner:

The crude product is redissolved in acetonitrile (25 cc) for esterification with diphenyldiazomethane (0.4 g) for 1 hour at 20° C.; after concentration to 10 cc under reduced pressure (30 mm Hg; 4 kPa) at 30° C., the concentrate is taken up in ethyl acetate (100 cc) and the solution is washed with 4 N hydrochloric acid (50 cc) and then with a saturated solution of sodium bicarbonate (50 cc) and a saturated solution of sodium chloride (2×50 cc). After drying over magnesium sulphate, the solution is concentrated to dryness under reduced pressure (30 mm Hg; 4 kPa) at 30° C. and the residue is then chromatographed on a column (height: 20 cm, diameter: 2 cm) of silica gel (0.04–0.06 mm), elution being carried out under a pressure of 0.4 bar (40 kPa) with a mixture of cyclohexane and ethyl acetate (50/50 by volume), and 50 cc fractions being collected. Fractions 11 to 24, containing the pure product, are combined and concentrated to dryness under reduced pressure (30 mm Hg; 4 kPa) at 30° C. This gives 2-benzhydryloxycarbonyl-7-[(D)-α-t-butoxycarbonylamino-(4-hydroxyphenyl)-acetamido]-8-oxo-3-(thiazol-5-yl)-5-thia-1-azabicyclo[4.2.0]oct-2-ene (0.16 g) in the form of an amorphous yellow solid.

Infra-red spectrum (CHBr$_3$), characteristic bands (cm$^{-1}$): 3,560, 3,400, 3,330, 1,785, 1,720, 1,690, 1,610, 1,595, 1,490, 1,450, 1,390, 1,365, 1,220, 755.

Proton NMR spectrum (350 MHz, CDCl$_3$, α in ppm, J in Hz): 1.45 (s, 9H, —C(CH$_3$)$_3$); 3.43 and 3.63 (2d, J=18, 2H, —S—CH$_2$—); 5.03 (d, J=5, 1H, —H in the 6-position);

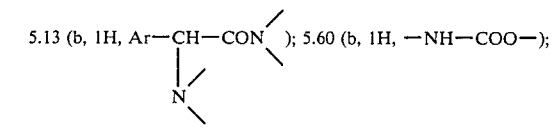

5.87 (dd, J=5 and 9, and b, 2H, —H in the 7-position and —OH); 6.62 (d, J=9, 1H, —CO—NH—); 6.77 (d, J=8, 2H, aromatic —H atoms in the ortho-positions to the —OH); 6.90 (s, 1H, —COO—CH(C$_6$H$_5$)$_2$); 7 to 7.4 (m, aromatic protons); 7.52 (s, 1H, =CH—N= of the thiazole); 8.56 (s, 1H, —N=CH—S— of the thiazole).

Following the procedure described below in Reference Example 10, 2-benzhydryloxycarbonyl-7-[(D)-α-t-butoxycarbonylamino-(4-hydroxyphenyl)-acetamido]-8-oxo-3-(thiazol-5-yl)-5-thia-1-azabicyclo[4.2.0]oct-2-ene (0.16 g) is treated with trifluoroacetic acid (5 cc); this gives 7-[(D)-α-amino-(4-hydroxyphenyl)-acetamido]-2-carboxy-8-oxo-3-(thiazol-5-yl)-5-thia-1-azabicyclo[4.2.0]oct-2-ene trifluoroacetate (0.082 g) in the form of a cream-coloured solid.

Infra-red spectrum (KBr), characteristic bands (cm$^{-1}$): 3,300–2,200, 1,775, 1,675, 1,610, 1,515, 1,200, 1,135, 840, 800, 720.

Proton NMR spectrum (350 MHz, d$_6$ DMSO δ in ppm, J in Hz): 3.73 and 3.82 (2d, J=18, 2H, —CH$_2$—S—);

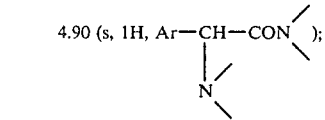

5.15 (s, J=5, 1H, —H in the 6-position); 5.84 (dd, J=5 and 9, 1H, —H in the 7-position); 6.80 (s, J=8, 2H, aromatic —H atoms in the ortho-positions to the —OH); 7.30 (d, J=8, 2H, aromatic —H atoms in the meta-positions to the —OH); 7.88 (s, 1H, =CH—N= of the thiazole); 8.60 (b, 3H, —NH$_3^⊕$); 9.06 (s, 1H, —N=CH—S—); 9.53 (d, J=9, 1H, —CO—NH—); 9.80 (b, 1H, —OH); 13.25 (b very spread out, —COOH).

By following the procedure of Reference Example 10, but starting from 7-[(D)-α-amino-(4-hydroxyphenyl)-acetamido]-2-carboxy-8-oxo-3-(thiazol-5-yl)-5-thia-1-azabicyclo[4.2.0]oct-2-ene trifluoroacetate (3.9 g) and by treatment with Amberlite IR 45 resin (in the OH$^-$form) (25 cc) in distilled water (100 cc), followed by filtration and lyophilisation, 7-[(D)-α-amino-(4-hydroxyphenyl)-acetamido]-2-carboxy-8-oxo-3-(thiazol-5-yl)-5-thia-1-azabicyclo[-4.2.0]oct-2-ene (internal salt) (1.6 g) is obtained in the form of a white lyophilisate.

Infra-red spectrum (KBr), characteristic bands (cm$^{-1}$): 3,300–2,200, 1,765, 1,690, 1,610, 1,520, 1,390, 1,250, 840.

The proton NMR spectrum (CF₃CO₂D) is identical to that of the trifluoroacetate, run under the same conditions.

REFERENCE EXAMPLE 6

The product of Example 2 can be used in the following manner:

N-Phenylthiourea (3.34 g) is added to a solution of 2-benzhydryloxycarbonyl-7-t-butoxycarbonylamino-3-(1-chloro-2-oxoethyl)-8-oxo-5-thia-1-azabicyclo[4.2.0]oct-2-ene (mixture of the epimers of the chloroaldehyde) (10.3 g) in a mixture of tetrahydrofuran (100 cc) and ethanol (40 cc), and the reaction mixture is then heated at the reflux temperature for 135 minutes. It is diluted with ethyl acetate (250 cc) and a semi-saturated solution of sodium bicarbonate (500 cc). The organic layer is washed with a semi-saturated solution of sodium chloride (250 cc) and then dried over magnesium sulphate and concentrated to dryness under reduced pressure (30 mm Hg; 4 kPa) at 30° C. The residue obtained is chromatographed on a column (height: 30 cm; diameter: 7 cm) of silica gel (0.04–0.06 mm), elution being carried out under a pressure of 0.7 bar (70 kPa) with a 70/30 (by volume) mixture of cyclohexane and ethyl acetate. After 1.5 liters of eluate have been collected, 100 cc fractions are collected and fractions 20 and 21 are combined and concentrated to dryness under reduced pressure (30 mm Hg; 4 kPa) at 30° C. The residue is triturated in isopropyl ether (30 cc). This gives 3-(2-anilinothiazol-5-yl)-2-benzhydryloxycarbonyl-7-t-butoxycarbonylamino-8-oxo-5-thia-1-azabicyclo[4.2.0]oct-2-ene (2.7 g) in the form of a yellow solid.

Infra-red spectrum (CHBr₃), characteristic bands (cm⁻¹): 3,420, 1,785, 1,720, 1,600, 1,540, 1,500, 1,495, 1,455, 1,390, 1,370, 750.

Proton NMR spectrum (350 MHz, CDCl₃, α in ppm, J in Hz): 1.47 (s, 9H, —C(CH₃)₃); 3.52 and 3.67 (2d, J=18, 2H, —S—CH₂—); 5.03 (d, J=4.5, 1H, —H in the 6-position); 5.41 (d, J=9, 1H, —CO—NH—); 5.66 (dd, J=4.5 and 9, 1H, —H in the 7-position); 6.95 (s, 1H, —COO—CH(C₆H₅)₂); 7.05 (s, 1H, —H of the thiazole); 7.05 to 7.4 (m, 15H, aromatic protons); 8.91 (s broad, 1H, —NH—).

3-(2-Anilinothiazol-5-yl)-2-benzhydryloxycarbonyl-7-t-butoxycarbonylamino-8-oxo-5-thia-1-azabicyclo[4.2.0]oct-2-ene (2.3 g) is treated with methanesulphonic acid (2.3 cc) in acetonitrile (23 cc) by following the procedure described in Reference Example 1. This gives crude 7-amino-3-(2-anilinothiazol-5-yl)-2-benzhydryloxycarbonyl-8-oxo-5-thia-1-azabicyclo[4.2.0]oct-2-ene (1.85 g), which is acylated with (thien-2-yl)-acetyl chloride (0.445 cc) in tetrahydrofuran (25 cc), in the presence of triethylamine (0.505 cc), by following the procedure described in Reference Example 1. The crude product obtained is chromatographed on a column (height: 30 cm; diameter: 2.5 cm) of silica gel (0.04–0.06 mm), elution being carried out under a pressure of 1.2 bars (120 kPa) with a 70/30 (by volume) mixture of cyclohexane and ethyl acetate (3 liters), and 50 cc fractions being collected. Fractions 20 to 50 are combined and concentrated to dryness. After trituration in isopropyl ether, 3-(2-anilinothiazol-5-yl)-2-benzhydryloxycarbonyl-8-oxo-7-(thien-2-yl-acetamido)-5-thia-1-azabicyclo[4.2.0]oct-2-ene (0.9 g) is obtained in the form of a yellow solid.

Infra-red spectrum (KBr), characteristic bands (cm⁻¹): 3,380, 1,785, 1,720, 1,675, 1,600, 1,530, 1,500, 1,455, 750, 700, 620, 605.

Proton NMR spectrum (350 MHz, CDCl₃, δ in ppm, J in Hz): 3.51 (limiting AB system, 2H, —S—CH₂-); 3.84 (s, 2H, —CH₂—CO—N<); 5.04 (d, J=4.5, 1H, —H in the 6-position); 5.84 (dd, J=4.5 and 9, 1H, —H in the 7-position); 6.92 (s, 1H, —COO—CH(C₆H₅)₂); 6.95 to 7.03 (m, 2H, =CH—CH= of the thiophene); 7.05 to 7.40 (m, 18H, aromatic protons, —H of the thiazole, =CH—S— of the thiophene and —CO—NH—); 8.65 (b, 1H, —NH—).

3-(2-Anilinothiazol-5-yl)-2-benzhydryloxycarbonyl-8-oxo-7-(thien-2-yl-acetamido)-5-thia-1-azabicyclo[4.2.0]oct-2-ene (0.9 g) is treated with formic acid (9 cc) by following the procedure described in Reference Example 1, and 3-(2-anilinothiazol-5-yl)-2-carboxy-8-oxo-7-(thien-2-yl-acetamido)-5-thia-1-azabicyclo[4.2.0]oct-2-ene (0.4 g) is obtained in the form of a yellow solid.

Infra-red spectrum (KBr), characteristic bands (cm⁻¹): 3,400, 3,280, 3,150–2,000, 1,770, 1,665, 1,625, 1,605, 1,530, 1,500, 1,455, 1,400, 750, 700.

Proton NMR spectrum (350 MHz, d₆-DMSO, δ in ppm, J in Hz): 3.79 (limiting AB system, 2H, —CH₂CO—N<); 3.76 and 3.87 (2d, J=18, 2H, —S—CH₂—); 5.16 (d, J=5, 1H, —H in the 6-position); 5.68 (dd, J=5 and 9, 1H, —H in the 7-position); 6.85 to 7 (m, 2H, =CH—CH= of the thiophene); 7.20 to 7.4 (m, 5H, aromatic —H in the metapositions and para-position of the anilino, =CH—S— of the thiophene and —H of the thiazole); 7.58 (d, J=7.5, 2H, aromatic —H atoms in the ortho-positions of the anilino); 9.15 (d, J=9, 1H, —CO—NH—); 10.27 (s broad, 1H, —NH—).

REFERENCE EXAMPLE 7

The product of Example 5 can be used in the following manner:

A solution of thiourea (1.23 g) in a mixture of tetrahydrofuran (8 cc) and water (1.6 cc) is added, over a period of 10 minutes, to the reaction mixture of Example 5, kept at −20° C., and the temperature is then allowed to rise to 20° C., with stirring for 30 minutes. The mixture is then transferred into a separating funnel containing ethyl acetate (300 cc) and washed with a semi-saturated solution of sodium bicarbonate (250 cc), water (250 cc) and a saturated solution of sodium chloride (250 cc). The organic phase is then dried over anhydrous sodium sulphate; it is filtered and the filtrate is concentrated to dryness under reduced pressure (30 mm Hg; 4 kPa) at 40° C. The residue (6.48 g) is chromatographed on silica gel (0.04–0.06 mm), elution being carried out under 40 kPa with a 30/70 (by volume) cyclohexane/ethyl acetate mixture, and 60 cc fractions being collected. Fractions 12 to 21, containing the product, are combined and the eluant is evaporated off under reduced pressure (30 mm Hg; 4 kPa) at 40° C. This gives 3-(2-aminothiazol-5-yl)-2-benzhydryloxycarbonyl-8-oxo-7-tritylamino-5-oxa-1-azabicyclo[4.2.0]oct-2-ene (0.65 g) in the form of a hard, light brown foam.

Infra-red spectrum (KBr), characteristic bands (cm⁻¹): 1,790, 1,725, 1,490, 1,220, 745, 700.

Proton NMR spectrum (350 MHz, CDCl₃, δ in ppm, J in Hz): 3.12 (d, J=10, 1H, —NH—C(C₆H₅)₃); 3.85 (d, J=3.5, 1H, —H in the 6-position); 4.05 and 4.50 (2d, J=18, 2H, —CH₂—O—); 4.39 (dd, J=3.5 and 10, 1H, —H in the 7-position); 4.88 (b, 2H, —NH₂); 6.91 (s, COOCH(C₆H₅)₂, —H of the thiazole); 7.10 to 7.65 (m, aromatic protons).

A solution of acetyl chloride (0.11 g) in dry tetrahydrofuran (2 cc) is added, over a period of 3 minutes, to a solution, cooled to 0° C., of 3-(2-aminothiazol-5-yl)-2- benzhydryloxycarbonyl-8-oxo-7-tritylamino-5-oxa-1-azabicyclo[4.2.0]oct-2-ene (0.80 g) in dry tetrahydrofuran (10 cc), and a solution of triethylamine (0.18 cc) in dry tetrahydrofuran (2 cc) is then added. The mixture is stirred for 30 minutes at 0° C. and then filtered on diatomaceous earth. The filtrate is diluted with ethyl acetate (50 cc) and washed with distilled water (50 cc), a semi-saturated solution of sodium bicarbonate (50 cc) and a saturated solution of sodium chloride (50 cc). The organic phase is dried over anhydrous sodium sulphate; it is filtered, the insoluble material is washed with ethyl acetate (10 cc) and the organic solution is concentrated under reduced pressure (30 mm Hg; 4 kPa). The residue (0.89 g) is chromatographed on a column (height: 24 cm; diameter: 2.2 cm) of silica (0.04–0.06 mm), elution being carried out with a 40/60 (by volume) cyclohexane/ethyl acetate mixture under 0.4 kPa, and 60 cc fractions being collected. Fractions 5 to 11 are combined and the solvent is evaporated off under reduced pressure (30 mm Hg; 4 kPa) at 40° C. This gives 3-(2-acetylaminothiazol-5-yl)-2-benzhydryloxycarbonyl-8-oxo-7-tritylamino-5-oxo-1-azabicyclo[4.2.0]oct-2-ene (0.55 g) in the form of a hard, light brown foam.

Infra-red spectrum (KBr), characteristic bands (cm$^{-1}$): 3,340, 1,790, 1,725, 1,700, 1,540, 1,210.

Proton NMR spectrum (350 MHz, CDCl$_3$, δ in ppm, J in Hz): 2.16 (s, 3H, <N—CO—CH$_3$); 3.14 (d, J=10, 1H, —NH-C(C$_6$H$_5$)$_3$); 3.89 (d, J=3.5, 1H, 13 H in the 6-position); 4.05 and 4.48 (d, J=18, 2H, —CH$_2$—O—); 4.43 (dd, J=10 and 3.5, 1H, —H in the 7-position); 6.86 (s, 1H, —COOCH(C6H5)$_2$; 7.10 (s, 1H, —H of the thiazole); 7.10 to 7.65 (m, aromatic protons); 10.93 (b, 1H, —NH—CO—CH$_3$).

A solution of 3-(2-acetylaminothiazol-5-yl)-2-benzydryloxycarbonyl-8-oxo-7-tritylamino-5-oxa-1-azabicyclo[4.2.0]oct-2-ene (0.54 g) and para-toluenesulphonic acid monohydrate (0.14 g) in acetone (5 cc) is heated under reflux for 3 hours. The reaction mixture is diluted with ethyl acetate (10 cc), washed with a semi-saturated solution of sodium bicarbonate (10 cc) and then with a saturated solution of sodium chloride (10 cc) and then dried over anhydrous sodium sulphate. It is filtered, the insoluble material is washed with ethyl acetate (2×5 cc) and the organic solution is concentrated to dryness under reduced pressure (3 mm Hg; 0.4 kPa) at 40° C. The residue (0.58 g) is a hard brown foam containing mainly 7-amino-3-(2-acetylaminothiazol-5-yl)-2-benzhydryloxycarbonyl-8-oxo-5-oxa-1-azabicyclo[4.2.0]oct-2-ene [Rf=0.11 (silica gel chromatography plate; eluant: cyclohexane/ethyl acetate, 20/80)]. A solution of thien-2-yl-acetylchloride (0.117 g) in tetrahydrofuran (1 cc) is added dropwise, over a period of 2 minutes, to a solution, cooled to 0° C., of the above product (0.58 g) in dry tetrahydrofuran (5 cc). The brown solution obtained is stirred at 0° C. for 5 minutes and a solution of triethylamine (0.073 g) in dry tetrahydrofuran (1 cc) is then added dropwise. The mixture is stirred for 1 hour 15 minutes at 0° C. It is then filtered and the filtrate is washed with a semi-saturated solution of sodium bicarbonate (25 cc), distilled water ( 25 cc) and a saturated solution of sodium chloride (25 cc). The organic phase is dried over anhydrous sodium sulphate; it is filtered and the insoluble material is then washed with ethyl acetate (2×5 cc). The organic solution is concentrated to dryness under reduced pressure (30 mm Hg; 4 kPa) at 40° C. and the residue is chromatographed on silica gel (0.2–0.06 mm) (diameter of the column: 1.4 cm; height of silica: 15 cm), elution being carried out with the following cyclohexane/ethyl acetate mixtures: 50/50 (500 cc), 40/60 (200 cc) and 30/70 (200 cc), and 15 cc fractions being collected. Fractions 40 to 49 are combined and the solvent is evaporated off under reduced pressure (30 mm Hg; 4 kPa) at 40° C. This gives 3-(2-acetylaminothiazol-5-yl)-2-benzhydryloxycarbonyl-8-oxo-7-(thien-2-yl)-acetamido-5-oxa-1-azabicyclo[4.2.0]oct-2-ene (0.1 g) in the form of a brown powder.

Proton NMR spectrum (350 MHz, CDCl$_3$, δ in ppm, J in Hz): 2.10 (s, 3H, <N—CO—CH$_3$); 3.90 (limiting AB system, —CH$_2$—CO—N<); 3.80 and 4.20 (m, —CH$_2$—O—); 5.04 (d, J=3.5, 1H, —H in the 6-position); 5.94 (dd, J=3.5 and 10, 1H, —H in the 7-position); 6.73 (s, 1H, —COO—CH(C$_6$H$_5$)$_2$); 6.8 to 6.95 (m, =CH—CH= of the thiophene); 6.9 to 7.6 (m, aromatic protons, —H of the thiazole and —S—CH= of the thiophene); 7.77 (b, 1H, —CO—NH—); 13.15 (b, 1H, —NH—CO—CH$_3$).

A solution of 3-(2-acetylaminothiazol-5-yl)-2-benzhydryloxycarbonyl-8-oxo-7-(thien-2-yl)-acetamido-5-oxa-1-azabicyclo[4.2.0]oct-2-ene (0.1 g) in formic acid (5 cc) is heated at 50° C. for 30 minutes, with stirring. The mixture is concentrated to dryness under reduced pressure (30 mm Hg; 4 kPa) at 50° C. and the residue is dissolved in ethanol (5 cc). The suspension obtained is stirred at 50° C. for 5 minutes and the solvent is evaporated off under reduced pressure (30 mm Hg; 4 kPa) at 50° C.; this operation is repeated once and the residue thus obtained is taken up in ethanol (2 cc). After filtration, the suspended solid gives 3-(2-acetylaminothiazol-5-yl)-2-carboxy-8-oxo-7-(thien-2-yl)-acetamido-5-oxo-1-azabicyclo[4.2.0]oct-2-ene (12 mg) in the form of a beige powder.

Infra-red spectrum (KBr), characteristic bands (cm$^{-1}$): 3,280, 3,100, 2,220, 1,790, 1,690, 1,655, 1,540, 1,515, 700.

Proton NMR spectrum (350 MHz, d$_6$-DMSO, δ in ppm, J in Hz): 2.14 (s, 3H, <N—CO—CH$_3$); 3.76 (s, 2H, —CH$_2$—CO—N<); 4.53 and 4.93 (2d, J=18, 2H, —CH$_2$—O—); 5.23 (d, J=3.5, 1H, —H in the 6-position); 5.58 (dd, J=3.5 and 9.5, 1H, —H in the 7-position); 6.85 to 7 (m, 2H, =CH—CH= of the thiophene); 7.35 (dd, =CH—S— of the thiophene); 7.61 (s, 1H, —H of the thiazole); 8.97 (d, J=9.5, 1H, —CO—NH—).

REFERENCE EXAMPLE 8

The product obtained in Example 9 can be used in the following manner:

A solution of acetyl chloride (1.51 cc) in dry tetrahydrofuran (10 cc) is added dropwise, over a period of 5 minutes, to a solution, cooled to 0° C., of 3-(2-aminothiazol-5-yl)-2-benzhydryloxycarbonyl-b 7-t-butoxycarbonylamino-8-oxo-5-thia-1-azabicyclo[4.2.0]oct-2-ene (10 g) in dry tetrahydrofuran (150 cc), and a solution of triethylamine (2.8 cc) in dry tetrahydrofuran (5 cc) is then added. The reaction mixture is stirred for 1 hour 30 minutes at about 0–5° C. and then treated again with acetyl chloride (1.51 cc) in tetrahydrofuran (10 cc). After 1 hour 50 minutes at 5° C., the reaction mixture is filtered and the filtrate is concentrated to 50 cc and diluted with ethyl acetate (250 cc). The organic phase is washed with a saturated solution of sodium bicarbonate (100 cc), distilled water (100 cc) and a semi-saturated solution of sodium chloride (100 cc) and then dried over magnesium sulphate and concentrated to dryness. This gives crude 3-(2-acetylaminothiazol-5-yl)-2-benzhydryloxycarbonyl-7-t-butoxycarbonylamino-8-oxo-5-thia-1-azabicyclo[4.2.0]oct-2-ene (10 g) in the form of a hard brown foam. By crystallisation from acetonitrile (25 cc), pure 3-(2-acetylaminothiazol-5-yl)-2-benzhydryloxycarbonyl-7-t-butoxycarbonylamino-8-oxo-5-thia-1-azabicyclo[4.2.0]oct-2-ene (5.9 g) is obtained in the form of a whitish crystalline powder, the characteristics of which are identical to those of the product obtained in Reference Example 1.

A solution of 3-(2-acetamidothiazol-5-yl)-2-benzhydryloxycarbonyl-7-t-butoxycarbonylamino-8-oxo-5-thia-1-azabicyclo[4.2.0]oct-2-ene (6.06 g) in acetonitrile (100 cc) is stirred with methanesulphonic acid (6 cc) for 30 minutes at 20° C. and then diluted with ethyl acetate (200 cc) and stirred with a saturated solution of sodium bicarbonate (300 cc). The aqueous layer is extracted with ethyl acetate (100 cc) and the combined organic solutions are washed with a semi-saturated solution of sodium chloride ($2 \times 250$ cc) and then dried over magnesium sulphate and concentrated to dryness under reduced pressure (30 mm Hg; 4 kPa) at 40° C. This gives 3-(2-acetamidothiazol-5-yl)-7-amino-2-benzhydryloxycarbonyl-8-oxo-5-thia-1-azabicyclo[4.2.0]oct-2-ene (4.9 g) in the form of a hard yellow foam. This product is redissolved in dry tetrahydrofuran (75 cc). The solution, cooled to about 0° C., is treated successively with phenylacetyl chloride (1.54 g) and with triethylamine (1.4 cc) and then stirred for 1 hour at between 0° and 4° C. The reaction mixture is diluted with ethyl acetate (100 cc) and a semi-saturated solution of sodium bicarbonate (200 cc). The organic layer is decanted, washed with water (100 cc) and then with a semi-saturated solution of sodium chloride (100 cc), dried over magnesium sulphate and concentrated to dryness under reduced pressure (30 mm Hg; 4 kPa) at 40° C. The residue is taken up in methylene chloride (25 cc). The precipitate is filtered off and then taken up in the boiling acetonitrile (80 cc). After cooling, the precipitate is filtered off, washed with acetonitrile (10 cc) and dried under reduced pressure (2 mm Hg; 0.27 kPa) at 25° C. This gives 3-(2-acetamidothiazol-5-yl)-2-benzhydryloxycarbonyl-8-oxo-7-phenylacetamido-5-thia-1-azabicyclo[4.2.0]octo-2-ene (2.65 g) in the form of a white solid.

Infra-red spectrum (KBr), characteristic bands (cm$^{-1}$): 3,410, 3,370, 3,170, 1,780, 1,730, 1,720, 1,700, 1,680, 1,655, 1,540, 1,525, 1,515, 1,495, 1,455, 1,230, 760, 740, 700.

Proton NMR spectrum (350 MHz, CDCl$_3$/d$_6$-DMSO, δ in ppm, J in Hz): 2.25 (s, 3H, >N—CO—CH$_3$); 3.57 and 3.68 (2d, J=14, 2H, —CH$_2$CON<); 3.63 and 3.75 (2d, J=18, 2H, —CH$_2$—S—); 5.14 (d, J=4.5, 1H, —H in the 6-position); 5.84 (dd, J=4.5 and 9, 1H, —H in the 7-position); 6.88 (s, 1H, —COO—CH(C$_6$H$_5$)$_2$); 7.12 (s, 1H, —H of the thiazole); 7 to 7.5 (m. 15H, aromatic protons); 9.08 (d, J=9, 1H, —CO—NH—); 11.95 (s broad, 1H, —NH—CO—CH$_3$).

3-(2-acetamidothiazol-5-yl)-2-benzhydryloxycarbonyl-8-oxo-7-phenylacetamido-5-thia-1-azabicyclo[4.2.0]oct-2-ene (2.65 g) is treated in a manner similar to that of Reference Example 1, and this gives the corresponding acid (1.7 g), which is purified in the following manner: the product is dissolved in a 5% strength solution of sodium bicarbonate. The aqueous solution is washed with ethyl acetate and then acidified to pH=4 with 1N hydrochloric acid. The precipitate is filtered off, washed with water (10 cc), ethanol (10 cc) and ethyl ether (10 cc) and dried. This gives 3-(2-acetamidothiazol-5-yl)-2-carboxy-8-oxo-7-phenylacetamido-5-thia-1-azabicyclo[4.2.0]oct-2-ene (1.55 g) in the form of a white solid.

Infra-red spectrum (KBr), characteristic bands (cm$^{-1}$): 3,280, 3,200, 3,100, 2,300, 1,785, 1,710, 1,695, 1,650, 1,540, 1,520, 1,495, 1,450.

Proton NMR spectrum (350 MHz, d$_6$-DMSO, δ in ppm, J in Hz): 2.18 (s, 3H, >N—CO—CH$_3$); 3.53 and 3.63 (2d, J=14, 2H, —CH$_2$—CO—N<); 3.78 and 3.93 (2d, J=18, 2H, —CH$_2$—S—); 5.17 (d, J=4.5, 1H, —H in the 6-position); 5.74 (dd, J=4.5 and 8, 1H, —H in the 7-position); 7.15 to 7.45 (m, 5H, aromatic protons); 7.52 (s, 1H, —H of the thiazole); 9.17 (d, J=9, 1H, —CO—NH—); 12.19 (s broad, 1H, —NH—CO—CH$_3$); 13.54 (b, 1H, —COOH).

REFERENCE EXAMPLE 9

The product obtained in Example 9 can be used in the following manner:

By treating 3-(2-aminothiazol-5-yl)-2-benzhydryloxycarbonyl-7-t-butoxycarbonylamino-8-oxo-5-thia-1-azabicyclo[4.2.0]oct-2-ene (4.5 g) with benzoyl chloride (1.11 cc) in dry tetrahydrofuran (55 cc), in the presence of triethylamine (1.23 cc), following the procedure of Reference Example 8, 3-(2-benzamidothiazol-5-yl)-2-benzhydryloxycarbonyl-7-t-butoxycarbonylamino-8-oxo-5-thia-1-azabicyclo[4.2.0]oct-2-ene (1.8 g) is obtained in the form of cream-coloured crystals.

Infra-red spectrum (KBr), characteristic bands (cm$^{-1}$): 3,420, 3,240, 1,790, 1,730, 1,705, 1,675, 1,600, 1,580, 1,545, 1,510, 1,500, 1,455, 1,370, 1,160, 760, 700.

Proton NMR spectrum (350 MHz, d$_6$-DMSO, δ in ppm, J in Hz): 1.45 (s, 9H, —C(CH$_3$)$_3$); 3.83 and 3.97 (2d, J=18, 2H, —CH$_2$—S—); 5.24 (d, J=5, 1H, —H in the 6-position); 5.67 (dd, J=5 and 9, 1H, —H in the 7-position); 6.91 (s, 1H, —COO—CH(C$_6$H$_5$)$_2$); 7.05 to 7.45 (m, 10H, aromatic protons); 7.49 (s, 1H, —H of the thiazole); 7.63 (t, J=7.5, 2H, aromatic protons in the meta-positions of the benzamido); 7.72 (t, J=7.5, 1H, aromatic proton in the para-position of the benzamido); 8.13 (d, J=9, 1H, —CO—NH—); 8.16 (d, J=7.5, 2H, aromatic protons in the ortho-positions of the benzamido); 12.72 (s, 1H, —NH—CO—C$_6$H$_5$).

A solution of 3-(2-benzamidothiazol-5-yl)-2-benzhydryloxycarbonylamino-7-t-butoxycarbonylamino-8-oxo-5-thia-1-azabicyclo[4.2.0]oct-2-ene (2.9 g) in the acetonitrile (29 cc) is treated with methanesulphonic acid (2.9 cc) by following the procedure of Reference Example 8. This gives crude 7-amine-3-(2-benzamidothiazol-5-yl)-2-benzhydryloxycarbonyl-8-oxo-5-thia-1-azabicyclo]4.2.0]oct-2-ene (2 g) in the form of a hard yellow foam.

Rf=0.22 (silica gel chromatography plate, eluant: mixture of cyclohexane and ethyl acetate, 30/70 by volume).

This product is taken up in dry tetrahydrofuran (50 cc) and acylated with (thien-2-yl)-acetyl chloride (0.53 cc), in the presence of triethylamine (0.6 cc), by following the procedure described in Reference Example 8. The crude product is chromatographed on a column (height: 22 cm; diameter: 4.4 cm) of silica gel (0.04–0.06 mm), elution being carried out under a pressure of 0.4 bar (40 kPa) with a mixture of cyclohexane and ethyl acetate (50/50 by volume), and 125 cc fractions being collected. Fractions 7 to 16, containing the pure product, are concentrated to dryness under reduced pressure (30 mm Hg; 4 kPa) at 30° C. This gives 3-(2-benzamidothiazol-5-yl)-2-benzhydryloxycarbonyl-8-oxo-7-(thien-2-yl-acetamido)-5-thia-1-azabicyclo[4.2.0]oct-2-ene (1.5 g) in the form of a hard yellow foam.

Infra-red spectrum (CHBr₃), characteristic bands (cm⁻¹): 3,400, 3,300, 2,500, 1,785, 1,725, 1,675, 1,600, 1,580, 1,535, 1,505, 1,490, 1,450, 755, 740.

Proton NMR spectrum (350 MHz, d₆-DMSO, δ in ppm, J in Hz): 3.74 and 3.81 (2d, J=14, 2H, —CH₂—CO—N<); 3.81 and 3.95 (2d, J=18, 2H, —CH₂—S—); 5.24 (d, J=5, 1H, —H in the 6-position); 5.82 (dd, J=5 and 8, —H in the 7-position); 6.84 (s, 1H, —COO—CH(C₆H₅)₂); 6.90 to 7 (m, 2H, =CH—CH= of the thiophene); 7 to 7.4 (m, 10H, aromatic protons); 7.35 (dd, J=4 and 1, 1H, =CH—S— of the thiophene); 7.42 (s, 1H, —H of the thiazole); 7.55 (t, J=7.5, 2H, aromatic protons in the meta-positions of the benzamido); 7.66 (t, J=7.5, 1H, aromatic proton in the para-position of the benzamido); 8.08 (d, J=7.5, 2H, aromatic protons in the ortho-positions of the benzamido); 9.23 (d, J=8, 1H, —CO—NH—); 12.60 (s, 1H, —NHCO—C₆H₅).

A solution of 3-(2-benzamidothiazol-5-yl)-2-benzhydryloxycarbonyl-8-oxo-7-(thien-2-yl-acetamido)-5-thia-1-azabicyclo[4.2.0]oct-2-ene (1.5 g) in a mixture of formic acid (43 cc) and distilled water (8 cc) is heated for 30 minutes at 60° C. and then diluted with distilled water (35 cc). The precipitate is filtered off, washed with 50% strength (by volume) formic acid (2×10 cc) and then with isopropyl ether (3×75 cc) and dried; this gives 3-(2-benzamidothiazol-5-yl)-2-carboxy-8-oxo-7-(thien-2-yl-acetamido)- 5-thia-1-azabicyclo[4.2.0]oct-2-ene (1 g) in the form of a white solid.

Infra-red spectrum (KBr), characteristic bands (cm⁻¹): 3,400, 3,260, 3,100, 2,100, 1,785, 1,665, 1,605, 1,585, 1,550, 1,495, 1,450, 705.

Proton NMR spectrum (350 MHz, d₆-DMSO, δ in ppm, J in Hz): 3.73 and 3.82 (2d, J=14, 2H, —CH₂—CO—N<); 3.80 and 3.95 (2d, J=18, 2H, —CH₂—S—); 5.20 (d, J=5, 1H, —H in the 6-position); 5.75 (dd, J=5 and 9, —H in the 7-position); 6.9 to 7 (m, 2H, =CH—CH= of the thiophene); 7.35 (dd, J=4 and 1, 1H, =CH—S— of the thiophene); 7.35 (t, J=7.5, 2H, aromatic protons in the meta-positions of the benzamido); 7.63 (s, 1H, —H of the thiazole); 7.64 (t, J=7.5, 1H, aromatic proton in the para-position of the benzamido); 8.10 (d, J=7.5 2H, aromatic protons in the ortho-positions of the benzamido); 9.18 (d, J=9, 1H, —CO—NH—); 11.60 (b, 1H, —COOH); 12.45 (b, 1H, —NH—CO—C₆H₅).

REFERENCE EXAMPLE 10

The product of Example 10 can be used in the following manner:

A solution of acetyl chloride (1.22 cc) in dry tetrahydrofuran (10 cc) is added, over a period of 5 minutes, to a solution, cooled to 4° C., of 3-(2-aminothiazol-5-yl)-2-benzhydryloxycarbonyl-7-[(D)-α-t-butoxycarbonylaminophenylacetamido]-8-oxo-5-thia-1-azabicyclo[4.2.0]oct-2-ene (10 g) in dry tetrahydrofuran (140 cc), and a solution of triethylamine (2.15 cc) in tetrahydrofuran (5 cc) is then added after 5 minutes. The reaction mixture is stirred for 4 hours at about 5° C. and then filtered, and the filtrate is partially concentrated and then poured into a mixture of ethyl acetate (200 cc) and a semi-saturated solution of sodium bicarbonate (200 cc); the organic phase is washed with water (2×100 cc) and with a saturated solution of chloride (100 cc) and then dried over magnesium sulphate. After evaporation of the solvent under reduced pressure (30 mm Hg; 4 kPa) at 40° C., the residue is crystallised from acetonitrile (80 cc) to give 3-(2-acetylaminothiazol-5-yl)-2-benzhydryloxycarbonyl-7-[(D)-α-t-butoxycarbonylaminophenylacetamido]-8-oxo-5-thia-1-azabicyclo[4.2.0]oct-2-ene (2.6 g) in the form of a light beige crystalline powder.

Infra-red spectrum (CHBr₃), characteristic bands (cm⁻¹): 3,400, 3,260, 3,160, 1,780, 1,715, 1,690, 1,560, 1,500, 1,490, 1,450, 1,390, 1,370, 760, 740.

Proton NMR spectrum (350 MHz, d₆-DMSO, δ in ppm, J in Hz): 1.4 (s, 9H, —C(CH₃)₃); 2.13 (s, 3H, —CO—CH₃); 3.67 and 3.81 (2d, J=18, 2H, —S—CH₂—); 5.12 (d, J=5, 1H, —H in the 6-position);

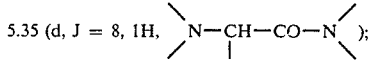

5.35 (d, J = 8, 1H, \N—CH—CO—N/ );

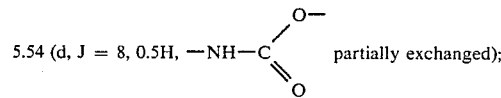

5.54 (d, J = 8, 0.5H, —NH—C(=O)O— partially exchanged);

5.83 (dd, J=5 and 9, 1H, —H in the 7-position); 6.82 (s, 1H, —COO—CH(C₆H₅)₂); 7 to 7.5 (m, 16H, aromatic protons and —H of the thiazole); 9.26 (d, J=9, 1H, —CO—NH—); 12.04 (s, 1H, —NH—CO—CH₃).

3-(2-Acetylaminothiazol-5-yl)-2-benzhydryloxycarbonyl-7-[(D)-α-t-butoxycarbonylaminophenylacetamido]-8-oxo-5-thia-1-azabicyclo[4.2.0]oct-2-ene (2.25 g) is dissolved in trifluoroacetic acid (20 cc). The solution is stirred at 25° C. for 20 minutes and then concentrated to dryness under reduced pressure (5 mm Hg; 0.7 kPa) at 40° C. The residue is taken up in isopropyl ether (30 cc). The solution is again evaporated to dryness under reduced pressure (30 mm Hg; 4 kPa) at 40° C. This operation is repeated 4 times and the residue is then triturated in ethyl ether (100 cc) and then filtered off, washed with ethyl ether (3×30 cc) and then dried. This gives 3-(2-acetylaminothiazol-5-yl)-7-[(D)-α-aminophenylacetamido]-2-carboxy-8-oxo-5-thia-1-azabicyclo[4.2.0]oct-2-ene trifluoroacetate (1.45 g) in the form of a beige powder.

Infra-red spectrum (KBr), characteristic bands (cm⁻¹): 3,180, 3,100, 2,150, 1,755, 1,680, 1,455, 1,200, 800, 720, 700.

Proton NMR spectrum (350 MHz, d₆-DMSO, δ in ppm, J in Hz): 2.13 (s, 3H, —CO—CH₃); 3.66 and 3.78 (2d, J=18, 2H, —S—CH₂—);

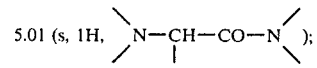

5.01 (s, 1H, \N—CH—CO—N/ );

5.11 (d, J=4.5, 1H, —H in the 6-position); 5.81 (b, 1H, —H in the 7-position); 7.35 to 7.65 (m, 6H, aromatic protons and —H of the thiazole), 8 to 10 (b spread out, 1H, —COOH); 9.58 (d, J=8, 1H, —CO—NH—); 12.14 (b, 1H, —NH—CO—CH₃).

This trifluoroacetate (1.2 g) is redissolved in water (100 cc) and the solution is washed with ethyl acetate (3×20 cc) and then decanted, treated with decolorising charcoal (0.5 g) and filtered, and the filtrate is stirred with Amberlite IR 45 resin (OH⁻) (washed beforehand with water until the washings are neutral) (20 cc) until the pH of the aqueous solution reaches 5.5. After removal of the resin by filtration, the aqueous solution is lyophilised. This gives 3-(2-acetylaminothiazol-5-yl)-7-[(D)-α-aminophenylacetamido]-2-carboxy-8-oxo-5-thia-1-azabicyclo[4.2.0]oct-2-ene (0.58 g) in the form of a white lyophilisate.

Infra-red spectrum (KBr), characteristic bands, (cm⁻¹): 3,240, 3,100, 2,300, 1,765, 1,685, 1,600, 1,545, 1,510, 1,455, 1,370, 720, 700.

NMR spectrum (CF₃CO₂H) consistent with that of the trifluoroacetate.

REFERENCE EXAMPLE 11

The product of Example 6 can be used in the following manner:

Following the procedure of Reference Example 5, 2-benzhydryloxycarbonyl-3-(1-bromo-2-oxoethyl)-7-diethoxyphosphorylamino-8-oxo-5-thia-1-azabicyclo[4.2.0]oct-2-ene (mixture of the isomeric bromoaldehydes) (2.6 g) is treated with thioformamide (0.31 g) in dry tetrahydrofuran (20 cc), and the product obtained is chromatographed on a column (height: 25 cm; diameter: 2.5 cm) of silica gel (0.04–0.06 mm), elution being carried out under a pressure of 0.5 bar with ethyl acetate, and 20 cc fractions being collected. Fractions 6 to 22, containing the pure product, are combined and evaporated to dryness under reduced pressure (30 mm Hg; 4 kPa) at 30° C. This gives 2-benzhydryloxycarbonyl-7-diethoxyphosphorylamino-8-oxo-3-(thiazol-5-yl)-5-thia-1-azabicyclo[4.2.0]oct-2-ene (1.6 g) in the form of a hard yellow foam.

Infra-red spectrum (CHBr₃), characteristic bands (cm⁻¹): 3,390, 1,790, 1,730, 1,240, 1,020, 975, 760, 740.

Proton NMR spectrum (350 MHz, CDCl₃, δ in ppm, J in Hz): 1.36 and 1.38 (2t, J=7, 6H, —CH₃); 3.56 and 3.75 (2d, J=18, 2H, —CH₂—S—);

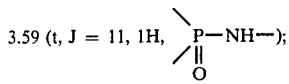

3.59 (t, J = 11, 1H, \P—NH—);

4.10 to 4.25 (m, 4H, —CH₂—O—); 5.06 (d, J= 5, 1H, —H in the 6-position); 5.22 (dt, J=5 and 11, 1H, —H in the 7-position); 6.89 (s, 1H, —COOCH(C₆H₅)₂); 7 to 7.4 (m, 10H, aromatic protons); 7.56 (s, 1H, =CH—N= of the thiazole); 8.57 (s, 1H, —S—CH=N— of the thiazole).

A mixture of 2-benzhydryloxycarbonyl-7-diethoxyphosphorylamino-8-oxo-3-(thiazol-5-yl)-5-thia-1-azabicyclo[4.2.0]oct-2-ene (1.5 g) and 85% strength (by weight) phosphoric acid (5 cc) is stirred for 16 hours at 20° C. and then diluted with distilled water (30 cc) at 0° C. and filtered. The solid is washed with distilled water (3×3 cc). Sodium bicarbonate (20.9 g) and then acetone (40 cc) are added to the filtrate (with which the washings have been combined), cooled to 0° C. After cooling to 0° C., a solution of thien-2-yl-acetyl chloride (1.2 cc) in acetone (10 cc) is added and the reaction mixture is then stirred for 3 hours at 0° C., and then for 16 hours at 20° C. It is diluted with distilled water (200 cc) and ethyl acetate (150 cc) and the aqueous phase is decanted, washed with ethyl acetate (3×40 cc) and then cooled to 0° C. and acidified to pH=2, in the presence of ethyl acetate (100 cc), by adding 10N hydrochloric acid. The aqueous phase is extracted with ethyl acetate (2×50 cc). The combined organic solutions are washed with water (3×50 cc), dried over magnesium sulphate and concentrated to dryness under reduced pressure (30 mm Hg; 4 kPa) at 30° C. The residue is triturated in isopropyl ether (50 cc). This gives 2-carboxy-8-oxo-3-(thiazol-5-yl)-7-(thien-2-yl-acetamido)-5-thia-1-azabicyclo[4.2.0]oct-2-ene (0.2 g) in the form of a beige powder, the characteristics of which are identical to those of the product obtained in Reference Example 4.

REFERENCE EXAMPLE 12

The product of Example 7 can be used in the following manner:

Following the procedure of Reference Example 5, 2-benzhydryloxycarbonyl-3-(1-chloro-2-oxoethyl)-7-diethoxyphosphorylamino-8-oxo-5-thia-1-azabicyclo[4.2.0]oct-2-ene (mixture of the diastereoisomeric chloroaldehydes) (1.16 g) is treated with thioformamide (0.15 g) in tetrahydrofuran (10 cc), and the crude product obtained is chromatographed on a column (height: 25 cm; diameter: 2.5 cm) of silica gel (0.04–0.06 mm), elution being carried out under a pressure of 0.5 bar (50 kPa) with ethyl acetate, and 20 cc fractions being collected. Fractions 10 to 18, containing the pure product, are combined and evaporated to dryness under reduced pressure (30 mm Hg; 4 kPa) at 30° C. This gives 2-benzhydryloxycarbonyl-7-diethoxyphosphorylamino-8-oxo-3-(thiazol-5-yl)-5-thia-1-azabicyclo[4.2.0]oct-2-ene (0.8 g) in the form of a hard yellow foam, the characteristics of which are identical to those of the product obtained in Reference Example 11.

REFERENCE EXAMPLE 13

The product of Example 12 can be used in the following manner:

A solution of thiourea (0.054 g) in distilled water (1 cc) is added to a solution of 2-benzhydryloxycarbonyl-3-(1-bromo-2-oxoethyl)-7-(3,4-dichlorophenylthio)acetamido-8-oxo-5-thia-1-azabicyclo[4.2.0]oct-2-ene (mixture of the diastereoisomers at the substituent in the 3-position) (0.5 g) in tetrahydrofuran (10 cc), and the reaction mixture is then stirred for 17 hours at 25° C. before being poured into a mixture of distilled water (250 cc), a saturated solution of sodium bicarbonate (60 cc) and ethyl acetate (60 cc). The organic phase is washed with distilled water (3×30 cc) and then with a saturated solution of sodium chloride (30 cc) and dried over magnesium sulphate. The residue obtained after concentration of the solvent to dryness under reduced pressure (30 mm Hg; 4 kPa) at 30° C. is chromatographed on a column (height: 28 cm, diameter: 2 cm) of silica gel (0.04–0.063 mm), elution being carried out under a pressure of 0.5 bar (50 kPa) with a 30/70 by volume mixture of cyclohexane and ethyl acetate, and 15 cc fractions being collected. Fractions 7 to 10, containing the pure product, are combined and concentrated under reduced pressure (30 mm Hg; 4 kPa) at 30° C. to give 3-(2-aminothiazol-5-yl)-2-benzhydryloxycarbonyl-7-(3,4-dichlorophenylthio)acetamido-8-oxo-5-thia-1-azabicyclo[4.2.0]oct-2-ene (0.29 g) in the form of a hard, pale yellow foam.

Infra-red spectrum (CHCl₃), characteristic bands (cm⁻¹): 3,490, 3,390, 1,780, 1,725, 1,685, 1,600, 1,495, 1,460.

Proton NMR spectrum (350 MHz, CDCl₃, δ in ppm, J in Hz): 3.41 and 3.51 (2d, J=17.5, 2H, —SCH₂— of the ring); 3.60 and 3.68 (2d, J=16, 2H, —S—CH₂—CO—); 5.01 (d, J=5, 1H, H in the 6-position); 5.37 (s broad, 2H, —NH₂); 5.77 (dd, J=5 and 9, 1H, H in the 7-position); 6.85 (s, 1H, H in the 4-position of the thiazole); 6.92 (s, 1H, —CO₂CH<); 7.10 to 7.50 (m, 13H, aromatic protons); 7.73 (d, J=9, 1H, —CONH—).

3-(2-Acetylaminothiazol-5-yl)-2-benzhydryloxycarbonyl-7-(3,4-dichlorophenylthio)-acetamido-8-oxo-5-thia-1-azabicyclo[4.2.0]oct-2-ene and then 3-(2-acetylaminothiazol-5-yl)-2-carboxy-7-(3,4-dichlorophenylthio)-acetamido-8-oxo-5-thia-1-azabicyclo[4.2.0]-oct-2-ene are prepared by following a procedure analogous to the method described in Reference Example 10.

We claim:

1. A cephalosporin of the formula:

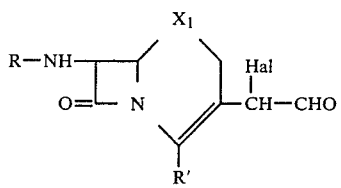

in which R' represents a protected carboxyl radical in which the protecting radical is chosen from t-butyl, methoxymethyl, 2,2,2-trichloroethyl, benzhydryl, p-nitrobenzyl and p-methoxybenzyl, Hal represents a halogen atom; and either (A) X₁ represents a sulphur or oxygen atom or a sulphinyl radical and R is a radical of the formula:

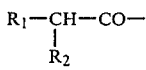

in which R₁ is a heterocyclic radical chosen from thienyl, furyl and 1,3-dithiol-2-on-4-yl, or a phenyl or phenoxy radical or a free or protected p-hydroxyphenyl radical in which the hydroxy-protecting radical is chosen from trityl, tetrahydropyranyl, alkoxycarbonyl, benzyloxycarbonyl and p-methoxybenzyl and R₂ is a hydrogen atom, or R₁ is a phenyl or free or protected p-hydroxyphenyl radical in which the hydroxy-protecting radical is chosen from trityl, tetrahydropyranyl, alkoxycarbonyl, benzyloxycarbonyl and p-methoxybenzyl and R₂ is a protected amino radical chosen from t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl and diphenylphosphinoyl and a group of the formula:

in which Z is an alkyl or 2,2,2-trichloroethyl group or a phenyl or benzyl group each of which is unsubstituted or substituted by a halogen atom or by an alkyl, alkoxy or nitro radical, or the symbols Z together form an alkylene radical containing 2 or 3 carbon atoms, or R is an amino-protecting radical which can easily be removed chosen from (1) benzhydryl or trityl, (2) an acyl radical of the formula:

in which R₃ represents (a) a hydrogen atom, alkyl of 1 to 7 carbon atoms, or methyl substituted by 1 to 3 halogen atoms, (b) phenyl, which is unsubstituted or substituted by up to three halogen atoms or hydroxyl, nitro, cyano, trifluoromethyl, alkyl or alkoxy radical, or thien-2-yl or thien-3-yl.

(c) a radical of the formula:

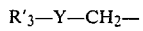

in which R'₃ is a phenyl radical which is unsubstituted or substituted by halogen or by alkyl, alkoxy or hydroxyl and Y is an oxygen or sulphur atom, or (d) a radical of the formula:

in which R''₃ is a phenyl radical which is unsubstituted or substituted by up to three hydroxyl, alkyl or alkoxy radicals, or a heterocyclic radical selected from thien-2-yl, thien-3-yl, furan-2-yl and furan-3-yl, (3) a 5-aminoadipoyl radical, the amino group of which is protected by a radical chosen from t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl and diphenylphosphinoyl and a group of the formula:

in which Z is an alkyl or 2,2,2-trichloroethyl group or a phenyl or benzyl group each of which is unsubstituted or substituted by a halogen atom or by an alkyl, alkoxy or nitro radical, or the symbols Z together form an alkylene radical containing 2 or 3 carbon atoms and the acid group of which is protected by a radical chosen from t-butyl methoxymethyl, 2,2,2-trichloroethyl, benzhydryl, p-nitrobenzyl and p-methoxybenzyl, (4) a radical of the formula:

in which R₄ is an unsubstituted branched alkyl radical, a linear or branched alkyl radical carrying one or more substituents chosen from halogen atoms or cyano, trialkylsilyl or phenyl radicals or phenyl radicals substituted by one or more halogen atoms or by alkyl, alkoxy nitro or phenyl radicals, or R₄ is a quinolyl radical, and (5) a radical of the formula:

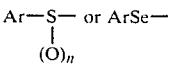

in which the radical Ar is a phenyl radical which is unsubstituted or substituted by one or more halogen atoms or alkyl or nitro radicals and n is 0 or 1, (6) or alternatively RNH— is replaced by a dialkylaminomethyleneamino radical or by a radical of the formula:

Ar'—CH=N— in which Ar' is a phenyl radical which is unsubstituted or substituted by one or more alkyl, alkoxy, hydroxyl or nitro radicals, (7) or R is a diphenylphosphinoyl radical or a radical of the formula:

in which Z is alkyl, 2,2,2-trichloroethyl, phenyl or benzyl, these last two being unsubstituted or substituted by a halogen atom or by alkyl, alkoxy or nitro, or the symbols Z together form an alkylene radical of 2 or 3 carbon atoms; or (B) $X_1$ represents a sulphur atom and R represents a radical of the formula:

R''—CO— in which R'' is an alkyl radical of 1 to 7 carbon atoms, or a cycloalkyl radical, or a radical chosen from benzyl, p-hydroxybenzyl, 4-amino-4-carboxybutyl (the amino group of which is protected by t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl, diphenylphosphinoyl, or by a group of the formula:

in which Z is an alkyl or 2,2,2-trichloroethyl group or a phenyl or benzyl group each of which is unsubstituted or substituted by a halogen atom or by an alkyl, alkoxy or nitro radical, or the symbols Z together form an alkylene radical containing 2 or 3 carbon atoms, and the acid group of which is protected by t-butyl, methoxymethyl 2,2,2-trichloroethyl, benzhydryl, p-nitrobenzyl or p-methoxybenzyl), 3-nitrobenzyl, 4-nitrobenzyl, phenethyl, 2-methoxyphenyl, 2-6-dimethoxyphenyl, protected p-aminobenzyl or protected o-aminobenzyl (in which the amino protecting group is chosen from t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl cr diphenylphosphinoyl and a group of the formula:

in which Z is an alkyl or 2,2,2-trichloroethyl group or a phenyl or benzyl group each of which is unsubstituted or substituted by a halogen atom or by an alkyl, alkoxy or nitro radical, or the symbols Z together form an alkylene radical containing 2 or 3 carbon atoms), p-methoxybenzyl, naphth-1-yl-methyl, isothiazol-3-yl-methyl, isothiazol-4-yl-methyl, isothiazol-5-yl-methyl, pyridin-4-yl-methyl, isoxazol-5-yl-methyl, benzofuranylmethyl, indol-2-yl-methyl, 3-methylimidazol-1-methyl, 5-methylthien-2-yl-methyl, 5-methylthien-3-yl-methyl, 5-methoxythien-2-yl-methyl, 5-methoxythien-3-yl-methyl, 4-chlorothien-2-yl-methyl, 4-chlorothien-3-yl-methyl, 1,2,5-thiadiazol-3-yl-methyl, 4-methoxy-1,2,5-thiadiazol-3-yl- methyl and tetrazolylmethyl;

or R is a radical of the formula:

R''—Y—(CH$_2$)$_m$—CO— in which m is an integer from 0 to 4, Y is an oxygen or sulphur atom and R'' is as defined above, or R is a radical of the formula:

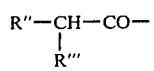

in which R'' is as defined above and R''' is a halogen atom or a hydroxy, protected hydroxy, azido, acyloxy, protected amino or protected carboxyl radical in which the hydroxy-protecting radical is chosen from trityl, tetrahydropyranyl, alkoxycarbonyl, benzyloxycarbonyl, and p-methoxybenzyl, the amino protecting radical is chosen from t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl or diphenylphosphinoyl and a group of the formula:

in which Z is an alkyl or 2,2,2-trichloroethyl group or a phenyl or benzyl group each of which is unsubstituted or substituted by a halogen atom or by an alkyl, alkoxy or nitro radical, or the symbols Z together form an alkylene radical containing 2 or 3 carbon atoms, and the carboxyl-protecting radical is chosen from t-butyl, methoxymethyl, 2,2,2-trichloroethyl, benzhydryl, p-nitrobenzyl and p-methoxybenzyl, or R—NH— represents a sulphonamido group, it being understood that the above-mentioned alkyl and acyl portions and radicals are linear or branched and are of 1 to 4 carbon atoms each, and the isomeric forms of the said cephalosporin and mixtures thereof.

2. A cephalosporin according to claim 1 in which
R' is benzhydryloxycarbonyl, p-nitrobenzyloxycarbonyl, t-butoxycarbonyl, methoxymethoxycarbonyl, 2,2,2-trichloroethoxycarbonyl, or p-methoxybenzyloxycarbonyl;

Hal is chlorine, bromine or iodine;

R is trityl, phenoxyacetyl, phenylacetyl, t-butoxycarbonyl, diethoxyphosphoryl, D-α-t-butoxycarbonylaminophenylacetyl, or 3,4-dichlorophenylthioacetyl; and $X_1$ is S, O, or >SO.

3. A cephalosporin according to claim 1 which is 2-benzhydryloxycarbonyl-3-(1-bromo-2-oxoethyl)-7-t-butoxycarbonylamino-8-oxo-5-thia-1-aza-bicyclo[4.2.0]-oct-2-ene in the form of epimer A or B or a mixture thereof.

4. A cephalosporin according to claim 1 which is 2-benzhydryloxycarbonyl-7-t-butoxycarbonylamino-3-(1-chloro-2-oxoethyl)-8-oxo-5-thia-1-aza-bicyclo[4.2.0]-oct-2-ene in the form of epimer A or B or a mixture thereof.

5. A cephalosporin according to claim 1 which is 3-(1-bromo-2-oxoethyl)-2-(4-nitrobenzyloxycarbonyl)-8-oxo-7-phenylacetamido-5-thia-1-aza-bicyclo[4.2.0]oct-2-ene in the form of epimer A or B or a mixture thereof.

6. A cephalosporin according to claim 1 which is 3-(1-bromo-2-oxoethyl)-2-(4-nitrobenzyloxycarbonyl)-8-oxo-7-phenoxyacetamido-5-thia-1-aza-bicyclo[4.2.0]-oct-2-ene in the form of epimer A or B or a mixture thereof.

7. A cephalosporin according to claim 1 which is 2-benzhydryloxycarbonyl-3-(1-bromo-2-oxoethyl)-8-oxo-7-tritylamino-5-oxa-1-azabicyclo[4.2.0]oct-2-ene in the form of epimer A or B or a mixture thereof.

8. A cephalosporin according to claim 1 which is 2-benzhydryloxycarbonyl-3-(1-bromo-2-oxoethyl)-7-diethoxyphosphorylamino-8-oxo-5-thia-1-azabicyclo[4.2.0]-oct-2-ene in the form of epimer A or B or a mixture thereof.

9. A cephalosporin according to claim 1 which is 2-benzhydryloxycarbonyl-3-(1-chloro-2-oxoethyl)-7-diethoxyphosphorylamino-8-oxo-5-thia-1-aza-bicyclo[4.2.0]-oct-2-ene in the form of epimer A or B or a mixture thereof.

10. A cephalosporin according to claim 1 which is 2-benzhydryloxycarbonyl-7-t-butoxycarbonylamino-3-(1-iodo-2-oxoethyl)-8-oxo-5-thia-1-aza-bicyclo[4.1.0]-oct-2-ene in the form of epimer A or B or a mixture thereof.

11. A cephalosporin according to claim 1 which is 2-benzhydryloxycarbonyl-3-(1-bromo-2-oxoethyl)-7-[(D)-α-t-butoxycarbonylaminophenylacetamido]-8-oxo-5-thia-1-aza-bicyclo[4.2.0]-oct-2-ene in the form of epimer A or B or a mixture thereof.

12. A cephalosporin according to claim 1 which is 2-benzhydryloxycarbonyl-3-(1-bromo-2-oxoethyl)-8-oxo-7-phenoxyacetamido-5-thia-1-azabicyclo[4.2.0]oct-2-ene in the form of epimer A or B or a mixture thereof.

13. A cephalosporin according to claim 1 which is 2-benzhydryloxycarbonyl-3-(1-bromo-2-oxoethyl)-7-(3,4-dichlorophenylthio)acetamido-8-oxo-5-thia-1-azabicyclo[4.2.0]oct-2-ene in the form of epimer A or B or a mixture thereof.

14. A cephalosporin according to claim 1 which is 2-benzhydryloxycarbonyl-3-(1-bromo-2-oxoethyl)-7-t-butoxycarbonylamino-8-oxo-5-thia-1-azabicyclo[4.2.0]oct-2-ene-5-oxide in the form of epimer A or B or a mixture thereof.

15. A cephalosporin according to claim 1 which is 2-benzhydryloxycarbonyl-7-butoxycarbonylamino-3-(1-chloro-2-oxoethyl)-8-oxo-5-thia-1-azabicyclo[4.2.0]oct-2-ene-5-oxide in the form of epimer A or B or a mixture thereof.

* * * * *